US006399392B1

(12) United States Patent
Haugland et al.

(10) Patent No.: US 6,399,392 B1
(45) Date of Patent: Jun. 4, 2002

(54) XANTHENE DYES AND THEIR APPLICATION AS LUMINESCENCE QUENCHING COMPOUNDS

(75) Inventors: Richard P. Haugland; Victoria L. Singer; Stephen T. Yue, all of Eugene, OR (US)

(73) Assignee: Molecular Probes, Inc., Eugene, OR (US)

( * ) Notice: Subject to any disclaimer, the term of this patent is extended or adjusted under 35 U.S.C. 154(b) by 0 days.

(21) Appl. No.: 09/556,464

(22) Filed: Apr. 21, 2000

Related U.S. Application Data

(60) Provisional application No. 60/130,808, filed on Apr. 23, 1999.

(51) Int. Cl.$^7$ .................... G01N 21/76; G01N 33/533; C07D 311/82; C07D 405/14
(52) U.S. Cl. ..................... 436/172; 435/6; 435/7.5; 435/188; 436/546; 436/800; 436/805; 530/402; 544/244; 546/173; 546/196; 546/199; 546/201; 546/208; 546/256; 548/156; 548/184; 548/455; 549/394
(58) Field of Search ................. 436/546, 172, 436/800, 805; 530/391.3, 402; 435/6, 7.5, 188; 549/227, 394; 548/525, 156, 184, 455; 544/244; 546/173, 196, 199, 201, 208, 256

(56) References Cited

U.S. PATENT DOCUMENTS

| | | |
|---|---|---|
| 4,256,882 A | 3/1981 | Friedrich et al. |
| 4,258,118 A | 3/1981 | Foley et al. |
| 4,439,359 A | 3/1984 | Holly et al. |
| 4,711,955 A | 12/1987 | Ward et al. |
| 4,720,449 A | 1/1988 | Borror et al. |
| 4,774,339 A | 9/1988 | Haugland et al. |
| 4,810,636 A | 3/1989 | Corey |
| 4,812,409 A | 3/1989 | Babb et al. |
| 5,047,519 A | 9/1991 | Hobbs, Jr. et al. |
| 5,134,432 A | 7/1992 | Haugland et al. |
| 5,187,288 A | 2/1993 | Kang et al. |
| 5,227,487 A | 7/1993 | Haugland et al. |
| 5,248,782 A | 9/1993 | Haugland et al. |

(List continued on next page.)

FOREIGN PATENT DOCUMENTS

| | | |
|---|---|---|
| DE | 23 37 488 | 1/1975 |
| DE | 24 60 491 | 7/1976 |
| DE | 26 57 217 | 6/1978 |
| DE | 33 47 246 | 7/1985 |
| EP | 0 542 420 | 5/1993 |
| EP | 0 745 690 | 12/1996 |
| EP | 0 805 190 | 11/1997 |
| GB | 2 067 215 | 7/1981 |
| GB | 2 311 075 | 9/1997 |
| JP | 58-97044 | 6/1983 |
| JP | 2-28263 | 2/1990 |
| JP | 9-255882 | 9/1997 |
| JP | 97/39064 | 10/1997 |
| WO | WO 97/39064 | 10/1997 |
| WO | WO 99/15517 | 4/1999 |
| WO | WO 99/16832 | 4/1999 |

OTHER PUBLICATIONS

Gulnik, S. V.; Suvorov, L. I.; Majer, P.; Collins, J.; Kane, B. P.; Johnson, D. G.; Erickson, J. W. *FEBS Lett* 1997, 413, 379–384.

Beekman, B.; van El, B.; Drijfhout, J. W.; Ronday, H. K.; TeKoppele, J.M., *FEBS Lett* 1997, 418, 305–309.

Beebe, K.D.; Pei, D. *Anal Biochem* 1998, 263, 51–56.

Haugland, Molecular Probes Handbook of Fluorescent Probes and Research Chemicals, Sixth Ed., Chapter 19 (1996).

Tyagi, et al., Nature Biotechnology 16, 49 (1998).

Molecular Probes Handbook of Fluorescent Probes and Research Chemicals, Sixth Ed., Richard P. Haugland, ed. (1996), in particular Chapters 1–3.

Bioprobes 26 (Oct. 1997).

Bioprobes 27 (Feb. 1998).

Bioprobes 28 (May 1998).

Bioprobes 29 (Nov. 1998).

Bioprobes 30 (Jan. 1999).

Gee, et al. Tet. Lett. 37, 7905 (1996).

Brinkley, Bioconjugate Chem., 3, 2 (1992).

Haugland, "Coupling of Monoclonal Antibodies with Fluorophores", Meth. Mol. Biol. vol. 45, 205 (1995).

The Molecular Probes Handbook of Fluorescence Probes and Research Chemicals, 1996, chapter 9.3.

Holskin, B. P.; Bukhtiyarova, M.; Dunn, B. M.; Baur, P.; Dechastonay, J.; Pennington, M. W. *Anal. Biochem* 1995, 226, 148–155.

Beekman, B.; Drijfhout, J. W.; Bloemhoff, W.; Ronday, H. K.; Tak, P. P.; te Koppele, J. M. *FEBS Lett* 1996, 390, 221–225.

Pennington, M. W., Thornberry, N. A. *Peptide Research* 1994, 7, 72–76.

Wang, Q. M.; Johnson, R. B.; Cohen, J. D.; Voy, G. T.; Richardson, J. M.; Jungheim, L. N.*Antivir Chem Chemother* 1997, 8, 303–310.

*Primary Examiner*—Mary E. Ceperley
(74) *Attorney, Agent, or Firm*—Allegra Helfenstein; Anton Skaugset; Elaine Stracker

(57) ABSTRACT

The quenching compounds of the invention are nitrogen-substituted xanthenes that are substituted by one or more aromatic or heteroaromatic quenching moieties. The quenching compounds of the invention exhibit little or no observable fluorescence and efficiently quench a broad spectrum of luminescent compounds. The chemically reactive quenching compounds possess utility for labeling a wide variety of substances, including biomolecules. These labeled substances are highly useful for a variety of energy-transfer assays and applications.

44 Claims, 1 Drawing Sheet

U.S. PATENT DOCUMENTS

| | | |
|---|---|---|
| 5,268,486 A | 12/1993 | Waggoner et al. |
| 5,274,113 A | 12/1993 | Kang et al. |
| 5,279,656 A | 1/1994 | Kenyon et al. |
| 5,433,896 A | 7/1995 | Kang et al. |
| 5,691,145 A | 11/1997 | Pitner et al. |
| 5,696,157 A | 12/1997 | Wang et al. |
| 5,714,327 A | 2/1998 | Houthoff et al. |
| 5,830,912 A | 11/1998 | Gee et al. |
| 5,846,726 A | 12/1998 | Nadeau et al. |
| 5,936,087 A | 8/1999 | Benson et al. |
| 6,130,101 A * | 10/2000 | Mao et al. |
| 6,162,931 A * | 12/2000 | Gee et al. |

* cited by examiner

XANTHENE DYES AND THEIR APPLICATION AS LUMINESCENCE QUENCHING COMPOUNDS

This application claims the priority of provisional application Ser. No. 60/130,808, filed Apr. 23, 1999, hereby incorporated by reference.

FIELD OF THE INVENTION

The invention relates to xanthene compounds that are efficient quenchers of luminescence, and their precursors. Chemically reactive versions of the xanthene compounds are described, as are conjugates prepared using the reactive compounds. Applications using the xanthene quenching compounds are also described.

BACKGROUND

Fluorescence Resonance Energy Transfer (FRET) is a process whereby a first fluorescent dye (the "donor" dye) is excited, typically by illumination, and transfers its absorbed energy to a second dye (the "acceptor" dye) that has a longer wavelength and therefore lower energy emission. Where the second dye is fluorescent, energy transfer results in fluorescence emission at the wavelength of the second dye. However, where the second dye is nonfluorescent, the absorbed energy does not result in fluorescence emission, and the fluorescence of the initial donor dye is said to be "quenched". Energy transfer can also be utilized to quench the emission of luminescent donors, including phosphorescent and chemiluminescent donors. When a luminescent emission is restored by preventing energy transfer, the luminescence is said to be "dequenched" or "unquenched".

The use of a variety of dyes to quench fluorescence is known in the art. The application of this phenomenon to analyze biological systems is also well-detailed. FRET has been utilized to study DNA hybridization and amplification, the dynamics of protein folding, proteolytic degradation, and interactions between other biomolecules (Methods in Enzymology, Vol. 278). By far the most common donor-acceptor dye pair utilized for these applications is dabcyl (the quenching dye) and EDANS (the fluorophore) (as discussed in The Molecular Probes Handbook of Fluorescence Probes and Research Chemicals, 1996, chapter 9.3). Selected examples of biological applications of FRET can be found in the following references, among others:

1) Holskin, B. P.; Bukhtiyarova, M.; Dunn, B. M.; Baur, P.; Dechastonay, J.; Pennington, M. W. *Anal Biochem* 1995, 227, 148–155.
(2) Beekman, B.; Drijfhout, J. W.; Bloemhoff, W.; Ronday, H. K.; Tak, P. P.; te Koppele, J. M. *FEBS Lett* 1996, 390, 221–225.
(3) Pennington, M. W.; Thomberry, N. A. *Peptide Research* 1994, 7, 72–76.
(4) Wang, Q. M.; Johnson, R. B.; Cohen, J. D.; Voy, G. T.; Richardson, J. M.; Jungheim, L. N. *Antivir Chem Chemother* 1997, 8, 303–310.
(5) Gulnik, S. V.; Suvorov, L. I.; Majer, P.; Collins, J.; Kane, B. P.; Johnson, D. G.; Erickson, J. W. *FEBS Lett* 1997, 413, 379–384.
(6) Beekman, B.; van El, B.; Drijfhout, J. W.; Ronday, H. K.; TeKoppele, J. M. *FEBS Lett* 1997, 418, 305–309.
(7) Beebe, K. D.; Pei, D. *Anal Biochem* 1998, 263, 51–56.

Despite. the widespread use of the dabcyl-EDANS energy transfer pair, this technology possesses a number of shortcomings. For most applications, the use of LW excitation is not optimal due to the autofluorescence exhibited by most cellular systems. Ultraviolet light can also cause DAN cross-linking in some systems. In addition, if LW excitation is used in a drug screening assay, many drugs, potential drugs, and biologically active proteins have very strong absorptions in the LV region. Both dabcyl and EDANS have low extinction coefficients, resulting in assays that are comparatively insensitive.

In order to avoid the difficulties associated with the use of ultraviolet excitation, the absorption of the energy acceptor should be closely aligned with the visible light fluorophore used. The compounds of the instant invention have been discovered to quench the fluorescence of a large variety of dyes, including dyes that are excited in the ultraviolet, but also including fluoresceins, rhodamines, and even longer wavelength fluorophores such as CY 5 and allophycocyanin. In addition, the compounds of the invention have significantly larger extinction coefficients than the quenching compounds that are typically currently used in energy transfer assays.

The compounds of the instant invention represent a new and highly useful class nonfluorescent energy acceptors, including chemically reactive versions, and the conjugates prepared therefrom.

SUMMARY OF THE INVENTION AND DESCRIPTION OF PREFERRED EMBODIMENTS

Figure 1:
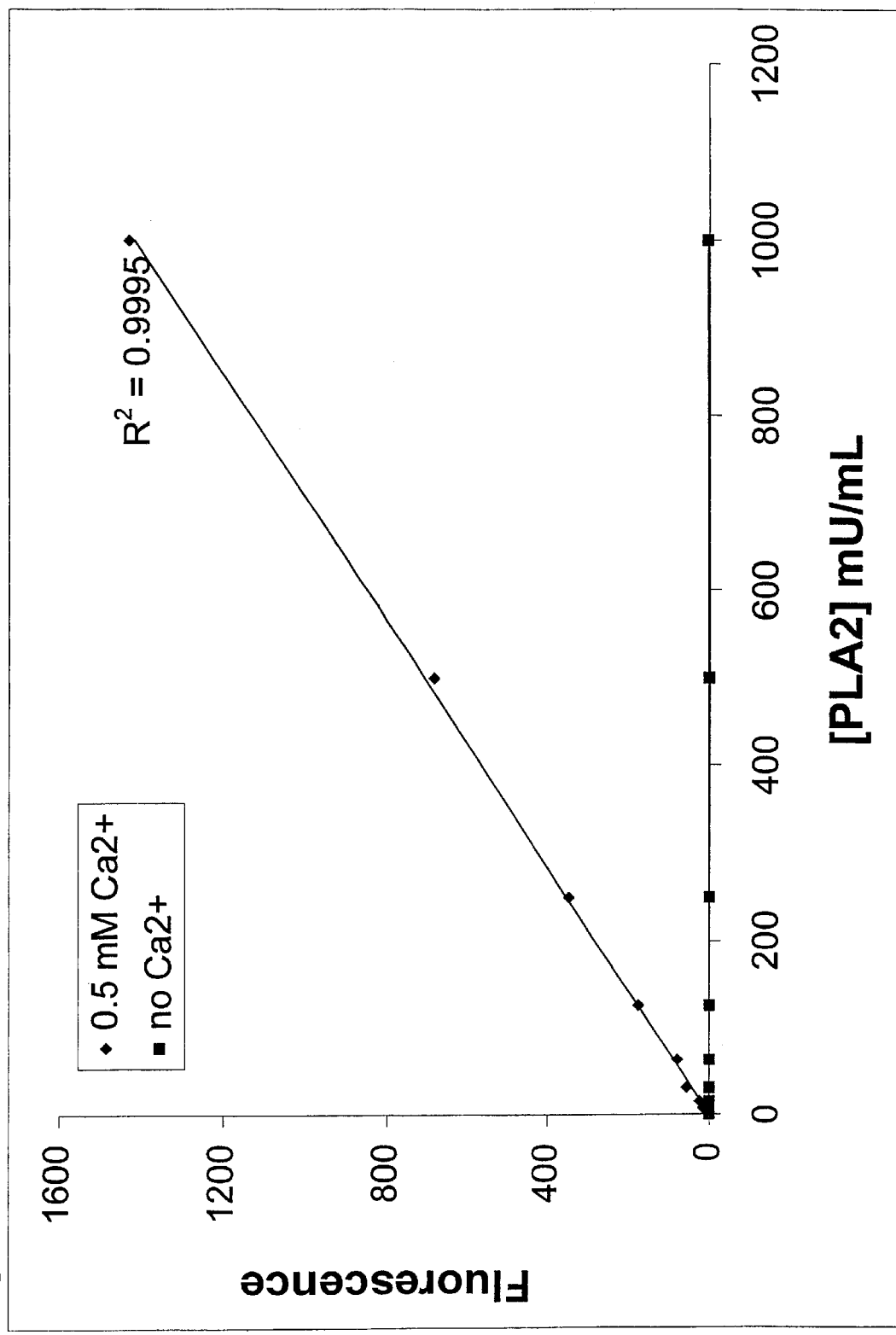
FIG. 1: Correlation of fluorescence intensity with phospholipase activity of $PLA_2$ (as described in Example 40).

The compounds of the invention are derivatives of 3- and/or 6-amino xanthenes that are substituted at one or more amino nitrogen atoms by an aromatic or heteroaromatic quenching moiety, Q. The quenching compounds of the invention have absorption maxima above 530 nm, have little or no observable fluorescence and efficiently quench a broad spectrum of luminescence, such as is emitted by chemilumiphores, phosphors, or fluorophores. In one embodiment, the quenching compound is a substituted rhodamine. In another embodiment, the quenching compound is a substituted rhodol. The chemically reactive quenching compounds possess utility for labeling a wide variety of substances, including biomolecules. These labeled substances are highly useful for a variety of energy-transfer assays and applications, particularly when used in combination with a luminophore.

As used herein, each quenching moiety, Q, is an aromatic or heteroaromatic ring system, having 1–4 fused aromatic or heteroaromatic rings, attached to the amino nitrogen by a single covalent bond. Where the Q moiety is fully aromatic and contains no heteroatom, Q comprises 1–4 fused six-membered aromatic rings. Where the Q moiety is heteroaromatic, Q incorporates at least one 5- or 6-membered aromatic heterocycle that contains at least 1 and as many as 4 heteroatoms that are selected from the group consisting of O, N, and S in any combination, that is optionally fused to an additional six-membered aromatic ring, or is fused to one 5- or 6-membered heteroaromatic ring that contains at least 1 and as many as 3 heteroatoms that are selected from the group consisting of O, N, and S in any combination.

Each Q moiety is bound to the xanthene compounds of the invention at a 3- or 6-amino nitrogen atom via a single covalent bond. In some embodiments, the amino nitrogen substituents, taken in combination, form a 5- or 6-membered heterocycle that is a piperidine, a morpholine, a pyrrolidine, a pyrazine, or a piperazine, and the Q moiety is fused to the resulting heterocycle adjacent to the xanthene nitrogen, so as to be formally bound to the amino nitrogen via single bond. The Q moiety may be bound to the amino nitrogen atom at either an aromatic or heteroaromatic ring, provided it is attached at a carbon atom of that ring.

Typically, the Q moieties of the invention are substituted or unsubstituted phenyl, naphthyl, anthracenyl, benzothiazole, benzoxazole, or benzimidazole. Where the amino nitrogen substituents form a 5- or 6-membered heterocycle and the Q moiety is fused to the resulting heterocycle, the heterocycle is typically a pyrrolidine ring and the Q moiety is typically a fused six-membered aromatic ring. Most preferably, Q is a phenyl or substituted phenyl.

Each Q moiety is optionally and independently substituted by hydrogen, halogen, cyano, sulfo, alkali or ammonium salt of sulfo, carboxy, alkali or ammonium salt of carboxy, nitro, alkyl, perfluoroalkyl, alkoxy, alkylthio, amino, monoalkylamino, dialkylamino or alkylamido.

The quenching compounds of the invention have the formula

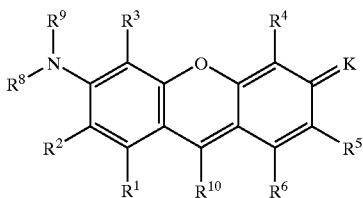

wherein the K moiety is O or N+$R^{18}R^{19}$.

For all the compounds of the invention, at least one of $R^8$, $R^9$, $R^{18}$ and $R^{19}$ is a Q moiety. Alternatively, either $R^8$ taken in combination with $R^9$, or $R^{18}$ taken in combination with $R^{19}$, forms a saturated 5- or 6-membered heterocycle that is a piperidine, or a pyrrolidine that is fused to a Q moiety. Typically one of $R^8$ and $R^9$ and one of $R^{18}$ and $R^{19}$ are each a Q moiety, which are the same or different. In another embodiment, each of $R^8$, $R^9$, $R^{18}$ and $R^{19}$ is a Q moiety, which may be the same or different.

The remainder of $R^8$, $R^9$, $R^{18}$, and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ aLkyl. Alternatively, where $R^8$ in combination with $R^9$, or $R^{18}$ in combination with $R^{19}$, or both, forms a saturated 5- or 6-membered heterocyclic ring that is a piperidine, a morpholine, a pyrrolidine, a pyrazine, or a piperazine, that is optionally substituted by methyl, sulfonic acid, a salt of sulfonic acid, carboxylic acid, a salt of carboxylic acid, or a carboxylic acid ester of a $C_1$–$C_6$ alkyl. Alternatively, one or more of $R^8$ in combination with $R^2$, $R^9$ in combination with $R^3$, $R^{18}$ in combination with $R^4$, or $R^{19}$ in combination with $R^5$, forms a 5- or 6-membered ring that is saturated or unsaturated, and that is optionally substituted by one or more $C_1$–$C_6$ alkyls or —$CH_2SO_3X$, where X is H or a counterion.

$R^1$ and $R^6$ are H, or one or more of $R^1$ in combination with $R^2$, or $R^6$ in combination with $R^5$, is a fused six-membered aromatic ring.

Substituents $R^2$, $R^3$, $R^4$, and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$.

The pendant group $R^{10}$ is H, CN, a carboxylic acid, a salt of carboxylic acid, or a carboxylic acid ester of a $C_1$–$C_6$ alcohol. Alternatively $R^{10}$ is a saturated or unsaturated, branched or unbranched $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino, the alkyl groups of which have 1–6 carbons. In another preferred embodiment, $R^{10}$ has the formula

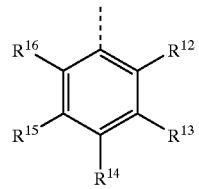

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino, azido; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_7$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons. Alternatively, a pair of adjacent substituents $R^{13}$ and $R^{14}$, $R^{14}$ and $R^{15}$, or $R^{15}$ and $R^{16}$, taken in combination, form a fused 6-membered aromatic ring that is optionally further substituted by carboxylic acid, or a salt of carboxylic acid.

The compounds of the invention are optionally substituted by a reactive group ($R_x$) or conjugated substance ($S_c$) that is attached to the compound of the invention by a covalent linkage, L. Typically, the compound of the invention is substituted by an —L—$R_x$ or —L—$S_c$ moiety at one or more of $R^8$, $R^9$, $R^{12}$, $R^{13}$, $R^{14}$, $R^{15}$, $R^{16}$, $R^{18}$, or $R^{19}$, preferably at one of $R^{12}$–$R^{16}$, most preferably at $R^{12}$, $R^{14}$ or $R^{15}$, or as a substituent on a Q moiety. Alternatively, an —L—$R_x$ or —L—$S_c$ moiety is present as a substituent on an alkyl, alkoxy, alkylthio or alkylamino substituent. In one embodiment, exactly one of $R^8$, $R^9$, $R^{12}$, $R^{13}$, $R^{14}$, $R^{15}$, $R^{16}$, $R^{18}$, or $R^{19}$ is an —L—$R_x$ or —L—$S_c$ moiety. In another embodiment, exactly one of $R^{12}$, $R^{13}$, $R^{14}$, $R^{15}$, or $R^{16}$ is an —L—$R_x$ or —L—$S_c$ moiety. In a preferred embodiment, one of $R^{12}$, $R^{14}$, and $R^{15}$ is an —L—$R_x$ or an —L—$S_c$ moiety.

Where the K moiety is N+$R^{18}R^{19}$, the compounds of the invention are rhodamines, and have the formula

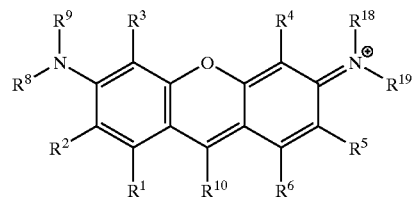

wherein at least one of $R^8$, $R^9$, $R^{18}$ and $R^{19}$ is a Q moiety. Preferably at least one of $R^8$ and $R^9$ is a Q moiety and at least one of $R^{18}$ and $R^{19}$ is a Q moiety, which may be the same or different.

Where the K moiety is O, the compounds of the invention are rhodols, and have the formula

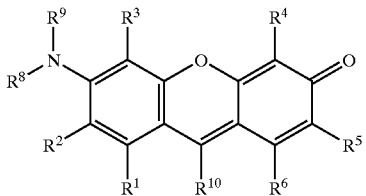

wherein at least one of $R^8$ and $R^9$ is a Q moiety.

Generally colorless forms of the instant compounds have the formula

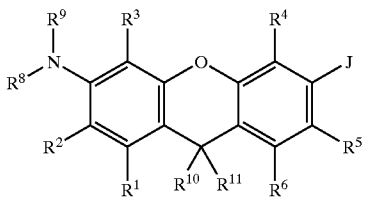

wherein J is O-$R^7$ or $NR^{18}R^{19}$, and $R^1$–$R^{19}$ is as defined above.

These precursors to the quenching compounds of the invention typically do not function as quenchers unless or until the aromaticity of the ring system is restored, as for the quenching compounds described above. In these precursors $R^7$ is H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl. Alternatively, $R^7$ is a monovalent radical formally derived by removing a hydroxy group from a carboxylic acid, a sulfonic acid, a phosphoric acid, or a mono- or polysaccharide, such as a glycoside. In another embodiment, $R^7$ is a photolabile caging group, such as described in Haugland, MOLECULAR PROBES HANDBOOK OF FLUORESCENT PROBES AND RESEARCH CHEMICALS, Sixth Ed., Chapter 19 (1996).

$R^{10}$ is as defined previously, and $R^{11}$ is H, hydroxy, CN or alkoxy having 1–6 carbons. Alternatively, $R^{10}$ in combination with $R^{11}$ forms a 5- or 6-membered spirolactone ring, or $R^{11}$ in combination with $R^{12}$ forms a 5- or 6-membered spirolactone ring, or a 5- or 6-membered sultone ring.

These precursor compounds are readily converted to the fully conjugated quenching compounds of the invention by chemical, enzymatic, or photolytic means. Typically, the colorless precursors are substituted by an —L—$R_x$ moiety, or are conjugated to a desired substance ($S_c$).

Conjugates of Reactive Compounds

In a preferred embodiment of the invention, the compound of the invention (quenching compound or precursor compound) is substituted by at least one group —L—$R_x$, where $R_x$ is the reactive group that is attached to the compound of the invention by a covalent linkage L. The compounds of the invention with a reactive group ($R_x$) label a wide variety of organic or inorganic substances that contain or are modified to contain functional groups with suitable reactivity, resulting in chemical attachment of the conjugated substance ($S_c$), represented by —L—$S_c$.

The reactive group and functional group are typically an electrophile and a nucleophile that can generate a covalent linkage. Typically, the conjugation reaction between the reactive compound and the substance to be conjugated results in one or more atoms of the reactive group $R_x$ to be incorporated into a new linkage L attaching the compound to the conjugated substance $S_c$. Selected examples of functional groups and linkages are shown in Table 2, where the reaction of an electrophilic group and a nucleophilic group yields a covalent linkage.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COW, where W is a good leaving group (e.g. succinimidyloxy (—O$C_4H_4O_2$) sulfosuccinimidyloxy (—O$C_4H_3O_2SO_3H$), -1-oxybenzotriazolyl (—O$C_6H_4N_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCO$R^a$ or OCN$R^a$NH$R^b$, where $R^a$ and $R^b$, which may be the same or different, are $C_1$–$C_6$ alkyl, $C_1$–$C_6$ perfluoroalkyl, or $C_1$–$C_6$ alkoxy; or cyclohexyl, 3-dimethylaminopropyl, or N-morpholinoethyl).
**Acyl azides can also rearrange to isocyanates The covalent linkage L binds the reactive group $R_x$ or conjugated substance $S_c$ to the compound, either directly (L is a single bond) or with a combination of stable chemical bonds, optionally including single, double, triple or aromatic carbon-carbon bonds, as well as carbon-nitrogen bonds, nitrogen-nitrogen bonds, carbon-oxygen bonds, carbonsulfur bonds, phosphorus-oxygen bonds, and phosphorus-nitrogen bonds. L typically includes ether, thioether, carboxamide, sulfonamide, urea, urethane or hydrazine moieties. In one embodiment, the covalent linkage incorporates a platinum atom, such as described in U.S. Pat. No. 5,714,327 (incorporated by reference). Preferred L moieties have 1–20 nonhydrogen atoms selected from the group consisting of C, N, O, P, and S; and are composed of any combination of ether, thioether, amine, ester, carboxamide, sulfonamide, hydrazide bonds and aromatic or heteroaromatic bonds. Preferably L is a combination of single carbon-carbon bonds and carboxamide or thioether bonds. The longest linear segment of the linkage L preferably contains 4–10 nonhydrogen atoms, including one or two heteroatoms. Examples of L include substituted or unsubstituted polymethylene, arylene, alkylarylene, arylenealkyl, or arylthio. In one embodiment, L contains 1–6 carbon atoms; in another, L is a thioether linkage. In yet another embodiment, L is or incorporates the formula $-(CH_2)_a(CONH(CH_2)_b)_z-$, where a has any value from 0–5, b has any value from 1–5 and z is 0 or 1.

Typically, $R_x$ will react with an amine, a thiol, an alcohol, an aldehyde or a ketone. In one embodiment, $R_x$ is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is meant chemically reactive platinum complexes such as described in U.S. Pat. No. 5,714,327 (incorporated by reference).

Preferably, $R_x$ is a phosphoramidite, a succinimidyl ester of a carboxylic acid, a haloacetamide, a hydrazine, an isothiocyanate, a maleimide group, a perfluorobenzamido, or an azidoperfluorobenzamido group. More preferably, $R_x$ is a phosphoramidite, a reactive platinum complex, or a succinimidyl ester of a carboxylic acid. Where $R_x$ is a reactive platinum complex, it is typically a haloplatinate.

Where the reactive group is a photoactivatable group, such as an azide, diazirinyl, azidoaryl, azidoperfluoroaryl, or a psoralen derivative, the compound of the invention typically becomes chemically reactive only after illumination with light of an appropriate wavelength.

Where $R_x$ is an activated ester of a carboxylic acid (such as a succinimidyl ester), the reactive compound of the invention is particularly useful for preparing conjugates of proteins, polysaccharides, lipids, nucleotides, or amino-modified oligonucleotides or haptens. Where $R_x$ is a maleimide or haloacetamide, the reactive compound of the invention is particularly useful for conjugation to thiol-containing substances. Where $R_x$ is a hydrazide, the reactive compound of the invention is particularly useful for conjugation to periodate-oxidized carbohydrates and glycoproteins. Where $R_x$ is a phosphoramidite, the reactive compound of the invention is particularly useful for the preparation of conjugates of oligonucleotides.

The reactive compounds of the invention are useful for the preparation of any conjugated substance that possess a suitable functional group for covalent attachment of the compound. Examples of particularly useful conjugates include, among others, conjugates of antigens, steroids, vitamins, drugs, haptens, metabolites, toxins, environmental pollutants, amino acids, peptides, proteins, nucleotides, oligonucleotides, nucleic acids (nucleic acid polymers), carbohydrates, lipids, ion-complexing moieties, and non-biological polymers. Preferably the conjugated substance is an amino acid, peptide, protein, nucleotide, oligonucleotide, or nucleic acid polymer. In particular, the conjugated substance is preferably a hapten or a member of a specific binding pair.

Choice of the reactive group used to attach the compound of the invention to the substance to be conjugated typically depends on the functional group on the substance to be conjugated and the type or length of covalent linkage desired. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. A given conjugated substance may be conjugated to one or more compound of the invention, which may be the same or different, or to a substance that is additionally modified by a hapten or specific binding pair member. Although some selectivity in cross-reactivity can be obtained by careful control of the reaction conditions, selectivity of labeling is best obtained by selection of an appropriate reactive functional group.

In a preferred embodiment, the conjugated substance is additionally conjugated to one or more luminophores, which may be the same or different. In one embodiment, energy transfer from the luminophores to the quenching compound occurs, resulting in significant quenching of luminescence. In another embodiment, the luminophore or luminophores are sufficiently distant from the quenching compound that energy transfer and therefore quenching is somewhat or substantially decreased. In yet another embodiment, the compound of the invention is a precursor to a quenching compound, and the emission of the luminophore or luminophores additionally bound to the conjugated substance is not quenched until conversion of the precursor to a quenching compound.

In one embodiment, the conjugated substance ($S_c$) is a natural or synthetic amino acid (including those that are protected or are substituted by phosphates, carbohydrates, or $C_1$ to $C_{22}$ carboxylic acids), or is a natural or synthetic polymer of amino acids such as a peptide or protein that is optionally derivatized by a chemical protecting group. Preferred conjugates of peptides contain at least five amino acids, more preferably 5 to 36 amino acids. Preferred peptides include, but are not limited to, neuropeptides, cytokines, toxins, protease substrates, and protein kinase substrates. Preferred protein conjugates include enzymes, antibodies, lectins, glycoproteins, histones, albumins, lipoproteins, avidin, streptavidin, protein A, protein G, phycobiliproteins and other fluorescent proteins (such as green fluorescent protein), hormones, toxins and growth factors. Typically, the conjugated protein is an antibody, an antibody fragment, an avidin, a streptavidin, a toxin, a lectin, a hormone, or a growth factor. Typically where the conjugated substance is a toxin, it is a neuropeptide or a phallotoxin, such as phalloidin. In another embodiment, the conjugated substance is a polypeptide or protein that is a substrate for an exopeptidase or an endopeptidase. Where the conjugated substance is a peptidase substrate that is simultaneously labeled with a luminophore or luminophores, the action of the peptidase enzyme cleaves the polypeptide, resulting in restoration of luminescence.

In another embodiment, the conjugated substance ($S_c$) is a natural or synthetic nucleic acid base, nucleoside, nucleotide or a nucleic acid polymer, including those that are protected, or modified to possess an additional linker or spacer for attachment of the compounds of the invention, such as an alkynyl linkage (U.S. Pat. No. 5,047,519), an aminoallyl linkage (U.S. Pat. No. 4,711,955) or other linkage. Preferably, the conjugated nucleotide is a nucleoside triphosphate or a deoxynucleoside triphosphate or a dideoxynucleoside triphosphate.

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates (AntiVirals, Inc., Corvallis Oreg.), or peptide nucleic acids such as N-(2-aminoethyl)glycine units. When the nucleic acid is a synthetic oligonucleotide, it typically contains fewer than 50 nucleotides, more typically fewer than 25 nucleotides. Larger nucleic acid polymers are typically prepared from labeled nucleotides or oligonucleotides using oligonucleotide-primed DNA polymerization, such as by using the polymerase chain reaction or through primer extension, or by terminal-transferase catalyzed addition of a labeled nucleotide to a 3'-end of a nucleic acid polymer. Typically, the compound of the invention is attached via one or more purine or pyrimidine bases through an amide, ester, ether or thioether bond; or is attached to the phosphate or carbohydrate by a bond that is an ester, thioester, amide, ether or thioether. Alternatively, the compound of the invention is bound to the nucleic acid polymer by chemical post-modification, such as with platinum reagents, or using a photoactivatable molecule such as a conjugated psoralen. In one embodiment, the quenching moiety is attached to the nucleotide, oligonucleotide or nucleic acid polymer via a phosphoramidite reactive group, resulting in a phosphodiester linkage. Alternatively, a conjugate of the invention is simultaneously labeled with a hapten such as biotin, digoxigenin, or 2,4-dinitrophenyl. Nucleotide conjugates of the invention are readily incorporated by a DNA polymerase.

In another embodiment, the conjugated substance ($S_c$) is a carbohydrate that is typically a natural or synthetic polysaccharide, such as a dextran, FICOLL, heparin, glycogen, amylopectin, mannan, inulin, starch, agarose and cellulose. The carbohydrates of the invention are optionally derivatized by protecting groups such as those used in carbohydrate synthesis. The conjugated carbohydrates are optionally further substituted by one or more luminophores, that are optionally the same or different. Alternatively, the carbohydrate is a polysaccharide that is a lipopolysaccharide. Preferred polysaccharide conjugates are dextran, starch, or FICOLL conjugates.

In another embodiment, the conjugated substance ($S_c$), is a lipid (typically having 6–60 carbons), including glycolipids, phospholipids, sphingolipids, glycerides, and steroids. Where the lipid is a phospholipid, the compound of the invention is preferably incorporated in the polar head group of the lipid. Alternatively, the conjugated substance is a lipid assembly, such as a liposome or a lipid droplet. Such a lipid assembly optionally comprises one or more additional luminophores.

Other conjugates of non-biological materials include conjugates of organic or inorganic polymers, polymeric films, polymeric wafers, polymeric membranes, polymeric particles, polymeric microparticles including magnetic and non-magnetic microspheres, conducting and non-conducting metals and non-metals, and glass and plastic surfaces and particles, which are optionally also conjugated to one or more luminophores, which may be the same or different. Conjugates are optionally prepared by copolymerization of a compound of the invention that contains an appropriate functionality while preparing the polymer, or by chemical modification of a polymer that contains functional groups with suitable chemical reactivity. Other types of reactions that are useful for preparing conjugates of polymers include catalyzed polymerizations or copolymerizations of alkenes, such as acrylamides, and reactions of dienes with dienophiles, transesterifications or transaminations. The compounds of the invention are optionally incorporated in polymers by polymerization of the monomer in the presence of the compound of the invention, resulting in non-covalent entrapment of the compound of the invention within the polymer matrix. In another embodiment, the conjugated substance is a glass or silica, which may be formed into an optical fiber or other structure.

Applications

The term "quenching compound" is used herein to refer to all aspects of the claimed quenching xanthenes, including rhodamine dyes and rhodol dyes, while "compound of the invention" is used to refer to both the quenching compounds of the invention and their colorless precursors.

In one aspect of the invention, the quenching compounds of the invention are useful simply as calorimetric labels for a conjugated substance. The compounds of the invention typically have large extinction coefficients, and thereby permit the detection of the quenching compound-conjugated substance by virtue of the visible light absorption of the quenching compound.

The quenching compounds of the present invention accept energy from a wide variety of luminophores, provided that the quenching compound and the luminophore are in sufficiently close proximity for quenching to occur, and that at least some spectral overlap occurs between the emission wavelengths of the luminophore and the absorption band of the quenching compound. This overlap may occur with emission of the donor occurring at a lower or even higher wavelength emission maximum than the maximal absorbance wavelength of the quenching compound, provided that sufficient spectral overlap exists. Energy transfer may also occur through transfer of emission of the donor to higher electronic states of the acceptor, such as from tryptophan residues of proteins to the weaker absorption bands between 300 and 350 nm typical of the dyes in the ultraviolet region. Preferably, the quenching compound of the invention is only dimly fluorescent, or essentially nonfluorescent, so that energy transfer results in little or no fluorescence emission. In one aspect of the invention, the quenching compound of the invention has a fluorescence quantum yield of less than about 0.05 (see, for example, Table 3). In another aspect of the invention, the quenching compound of the invention has a fluorescence quantum yield of less than about 0.01. In yet another aspect of the invention, the quenching compound of the invention has a fluorescence quantum yield of less than about 0.005.

Typically, quenching occurs through Fluorescence Resonance Energy Transfer between a donor and a quenching acceptor of the invention. The degree of FRET exhibited by a donor acceptor pair can be represented by the Forster equation:

$$R_o = (8.8 \times 10^{23} \cdot \kappa^2 \cdot n^{-4} \cdot QY_D \cdot J(\lambda))^{1/6} \text{Å}$$

wherein the Förster radius ($R_o$) represents the separation distance at which the energy transfer between a donor and acceptor is 50% efficient (i.e. 50% of excited donors are deactivated by FRET);

$\kappa^2$=dipole orientation factor (range 0–4, $\kappa^2=\frac{2}{3}$ for randomly oriented donors and acceptors);

$QY_D$=fluorescence quantum yield of the donor in the absence of the acceptor;

n=refractive index; and $J(\lambda)$=spectral overlap integral.

Because the degree of energy transfer is dependent on the spectral overlap integral, it can be readily appreciated that the spectral properties of the donor and acceptor dyes have a strong effect on the energy transfer observed, as shown in the following equation:

$$J(\lambda)=\int \epsilon_A(\lambda) \cdot F_D(\lambda) \cdot \lambda^4 d\lambda cm^3 M^{-1}$$

wherein $\epsilon_A (\lambda)$ is the absorption spectrum of the acceptor expressed in terms of molar extinction coefficient $\epsilon_A$. $F_D(\lambda)$ is the fluorescence emission spectrum of the donor, with the fluorescence intensity ($F_D$) expressed as a fraction of the total integrated intensity.

It should be readily appreciated that the degree of energy transfer during FRET, and therefore quenching, is highly dependent upon the separation distance between the luminophore and the quenching compound. In molecular systems, a change in luminescence quenching typically correlates well with a change in the separation distance between the luminophore molecules and the quenching compound molecules. Assays that detect such changes in luminescence are therefore useful for the detection of a great many structural changes, such as changes in molecular conformation, assembly of structures, or degradation of structures.

Any luminophore with sufficient spectral overlap with a quenching compound of the instant invention, as calculated above, is a suitable donor for the applications of the invention, other factors being equal. The greater the degree of overlap, the greater the overall quenching observed. While fluorescent dyes are preferred for energy transfer applications, any emission that generates light having sufficient spectral overlap with the quenching compounds of the invention is also useful, such as chemiluminescence, or phosphorescence, whether by FRET or by triplet state to singlet state transfer.

While FRET is the most common mechanism for quenching of fluorescence to occur, any combination of molecular orientation and spectral coincidence that results in quenching of luminescence is a useful mechanism for quenching by the quenching compounds of the invention, as described herein. For example, efficient quenching can occur even in the absence of spectral overlap if the luminophore and the quenching compound are sufficiently close together to form a ground-state complex (as described in Tyagi et al., NATURE BIOTECHNOLOGY 16,49 (1998)).

A wide variety of chemically reactive fluorescent dyes that would be suitable 25 luminophores (donors) are already known in the art (see for example MOLECULAR PROBES HANDBOOK OF FLUORESCENT PROBES AND RESEARCH CHEMICALS, Sixth Ed., Richard P. Haugland, ed. (1996), in particular Chapters 1–3; BIOPROBES 26 (October 1997); BIOPROBES 27 (February 1998); BIOPROBES 28 (May 1998); BIOPROBES 29 (November 1998); and BIOPROBES 30 (January 1999). The spectral properties of candidate dyes in solution or when conjugated to a selected biomolecule are known or are readily measured using a spectrofluorometer.

Typically, where the luminophore is a fluorophore, it is a fluorescent aromatic or heteroaromatic compound that is a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated derivatives thereof (as described in U.S. Pat. No. 5,830,912 to Gee et al. (1998), incorporated by reference), a polyazaindacene (such as 4-bora-3a,4a-diaza-s-indacene as described in U.S. Pat. No. 4,774,339 to Haugland, et al. (1988); U.S. Pat. No. 5,187,288 to Kang, et al. (1993); U.S. Pat. No. 5,248,782 to Haugland, et al. (1993); U.S. Pat. No. 5,274,113 to Kang, et al. (1993); and U.S. Pat. No. 5,433,896 to Kang, et al.(1995), all incorporated by reference), a xanthene, an oxazine or a benzoxazine, a carbazine (U.S. Pat. No. 4,810,636 to Corey (1989), incorporated by reference), or a phenalenone or benzphenalenone (U.S. Pat. No. 4,812,409 Babb et al. (1989), incorporated by reference). The donor dye is optionally an organic molecule that is a fluorophore, or a fluorescent protein such as a phycobiliprotein or "green fluorescent protein". Preferably, the donor dye is a carbazine, an oxazine, a coumarin, a pyrene, a xanthene, a naphthalene, a phenalenone, or a 4-bora-3a,4a-diaza-s-indacene. As used herein, oxazines include resorufins, aminooxazinones, diaminooxazines, and their benzo-substituted analogs. Preferred chemiluminescent dyes include luminol, isoluminol, luciferin, an acridinium ester, or a dioxetane.

Where the synthetic dye is a xanthene, the synthetic dye is optionally a fluorescein, a rhodol (U.S. Pat. No. 5,227,487 to Haugland, et al. (1993), incorporated by reference), or a rhodamine. As used herein, fluorescein includes benzo- or dibenzofluoresceins, seminaphthofluoresceins, or naphthofluoresceins. Similarly, as used herein rhodol includes seminaphthorhodafluors (U.S. Pat. No. 4,945,171 to Haugland, et al. (1990), incorporated by reference). Fluorinated xanthene dyes have also been described previously (Int. Publ. No. WO 97/39064, Molecular Probes, Inc. (1997)). Sulfonated pyrenes, coumarins, carbocyanines, and xanthene dyes have been described previously (U.S. Pat. No. 5,132,432 to Haugland et al., (1992); U.S. Pat. No. 5,696,157 to Wang et al. (1997); U.S. Pat. No. 5,268,486 patent to Waggoner et al. (1993); and Copending application Ser. No. 08/935,963 by Fei Mao et al., filed Sep. 23, 1997; all incorporated by reference).

Method of Use

The quenching compounds of the invention are useful in any application where energy transfer from a luminescent donor to a non-fluorescent acceptor has previously been described, provided that some spectral overlap exists between the emission of the donor dye and the absorbance of the quenching compound of the invention. Typically, the quenching compounds are used in combination with a luminophore in a method that detects a change in separation distance between the luminophore and the quenching compound.

The donor luminophores and quenching compounds used in the instant methods are useful in any medium in which they are sufficiently soluble. For example, selected embodiments of the instant quenching compounds that are substituted by highly non-polar substituents may be useful in organic solvents, or on or in non-polar matrices, such as polymeric microspheres. For biological applications, the quenching compounds of the invention and their conjugates are typically used in an aqueous, mostly aqueous or aqueous-miscible solution prepared according to methods generally known in the art.

Chemically reactive compounds of the invention will covalently attach to a corresponding functional group on a wide variety of materials, forming conjugates as described above. Photoreactive compounds of the invention can be used similarly to photolabel nucleic acids, or components of the outer membrane of biological cells, or as photo-fixable polar tracers for cells.

The quenching compounds of the invention are generally utilized by labeling a substance or sample of interest under conditions selected so that illumination of the sample with an appropriate wavelength of light results in a detectable optical response. In one embodiment, the quenching compounds of the invention are utilized as colorimetric labels, such that the detectable optical response is an absorption of illumination energy. In another embodiment the quenching compound accepts energy from a donor, such that the detectable optical response is quenching of the luminescence of the donor.

In most applications of the instant compounds, the labeled substance is utilized in a homogenous solution assay, where specific spatial resolution is not required. In these embodiments of the invention the loss of, or restoration of, luminescence in the sample is detected. In another embodiment, the quenching compound forms a covalent or non-covalent association or complex with an element of the sample where a luminescent component is present or is subsequently added. In this embodiment, illumination of the sample reveals either a luminescence response if quenching is not occurring, or the degree of quenching may be observed and correlated with a characteristic of the sample. Such correlation typically occurs by comparison with a standard or a calibration curve. Typically, a stained sample is illuminated and observed in order to determine a specified characteristic of the sample by comparing the degree of quenching exhibited to a luminescence standard of determined intensity. The luminescence standard may be a fluorescent dye such as the fluorophore used to prepare the quenching compound-fluorophore labeled substance, a luminescent particle (including fluorescent microspheres), a calibration curve prepared by assaying the doubly labeled substance with a known amount of enzyme or degradation activity, or any other standard that can be used to calibrate luminescence signal intensity as well known in the art.

Typically, the method of the invention comprises the steps of
a) illuminating the molecular system under study;
b) detecting the luminescence response of the system, which yields information as to the separation distance one or more luminophore donors and quenching compound acceptors;
c) exposing the molecular system to an environmental condition sufficient to change the separation distance, or thought to be sufficient to change the separation distance;
d) illuminating the molecular system again;
e) detecting the luminescence response of the molecular system again; and
f) comparing the first detected luminescence response to the second detected luminescence response, in order to determine a detectable difference in the detected luminescence before and after the exposure to the selected environmental condition. The detected change in the luminescence of the molecular system then correlates with any changes that occurred in the separation distance between the luminophores and the quenching compounds, typically in response to the selected environmental condition.

As discussed in greater detail below, the environmental condition of the instant method may be the presence of a particular enzyme, the presence of a complementary specific binding pair member, a change in pH, or a change in sample temperature.

Illumination and detection

Typically, changes in luminescence quenching are detected by methods well known in the art for standard luminescence assays. Sample luminescence, if present, is typically detected by illumination of the sample with a light source capable of producing light that is absorbed at or near the wavelength of maximum absorption of the donor dye, and luminescence is detected at a wavelength longer than the excitation wavelength, typically near the emission maximum. Such illumination sources include, but are not limited to, hand-held ultraviolet lamps, mercury-arc lamps, xenon lamps, lasers and laser diodes. These illumination sources are optionally integrated into laser scanners, fluorescence microplate readers, standard or minifluorometers, or chromatographic detectors.

The optical response is optionally detected by visual inspection, or by use of instrumentation, including CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal, such as photomultiplier tubes. Where the sample is examined using a flow cytometer, examination of the sample optionally includes sorting portions of the sample according to their luminescence response.

In the case of a sample in which the labeled substance is immobilized or partially immobilized on a solid or semi-solid support or in a matrix such as agar, sample luminescence is typically detected using a transilluminator, an epi-illuminator, a laser scanner, a microscope or a similar apparatus that permits observation of the matrix.

Luminescence occurring within a cell is typically detected using instrumentation that is capable of detecting luminescent emission in single cells, such as a microscope or a flow cytometer (optionally further being followed by sorting of luminescent cells). Alternatively, multiple cells are suspended and luminescence changes are measured as for an assay done in true solution.

Applications

As described above, the method of the instant invention is typically useful for detection of changes in separation distance between a luminophore donor and a quenching compound acceptor.

Any assay that relies upon the measurement of the proximity of luminophores and quenching compounds in a system may be carried out using the method of the instant invention. The method of the instant invention is typically utilized to detect and/or quantify the convergence or divergence of the luminophore donor and quenching compound acceptor. By convergence is meant a decrease in the average separation distance between the luminophore and the quenching compound. By divergence is meant an increase in the average separation distance between the luminophore and the quenching compound.

In one embodiment, the method of the instant invention is utilized to detect molecular or structural assembly (convergence). In another embodiment, the method of the invention is utilized to detect molecular or structural disassembly (divergence). In yet another embodiment, the method of the invention is utilized to detect a conformation change in a molecule, macromolecule or structure (optionally convergence or divergence). In yet another embodiment, the method of the instant invention incorporates aspects of the detection of assembly, disassembly, and/or conformation changes.

Detection of Structural Assembly

In one embodiment, the luminescence of a luminophore becomes quenched upon being placed in close proximity to a quenching compound of the invention (thereby decreasing the separation distance). The following systems, among others, can be analyzed using energy transfer pairs to detect and/or quantify structural assembly by measuring convergence of the donor and acceptor:

protein subunit assembly
enzyme-mediated protein assembly
molecular dimensions of proteins
membrane-protein interactions
protein-protein interactions
protein-protein-nucleic acid complex assembly
receptor/ligand interactions
immunoassays
nucleic acid hybridization
quantitative detection of specific DNA sequence amplification
detection of DNA duplex winding
nucleic acid-protein interactions
nucleic acid-drug interactions
primer extension assays for mutation detection
reverse transcriptase assay
strand exchange in DNA recombination reactions
membrane fusion assays
transmembrane potential sensing
ligation assays In particular, specific binding pair members labeled with a quenching compound are typically used as probes for the complementary member of that specific binding pair, by methods well known in the art. The complementary member is typically labeled with a luminescent label, and association of the two members of the specific binding pair results in luminescence quenching. This assay is particularly useful in nucleic acid hybridization assays, evaluation of protein-nucleic acid interaction, and in selected standard immunoassays. In one embodiment, a loss of luminescence indicates the association of an enzyme with an enzyme substrate, agonist or antagonist, such that the luminophore on one is brought into close proximity to a quenching compound on the other. Selected preferred specific binding pair members are proteins that bind non-covalently to low molecular weight ligands (including biotin), oligonucleotides, and drug-haptens. Representative specific binding pairs are shown in Table 1.

TABLE 1

Representative Specific Binding Pairs

| antigen | antibody |
| --- | --- |
| biotin | avidin, streptavidin, anti-biotin |
| folate | folate-binding protein |
| IgG* | protein A or protein G |
| drug | drug receptor |
| toxin | toxin receptor |
| carbohydrate | lectin or carbohydrate receptor |
| peptide | peptide receptor |
| protein | protein receptor |
| peptide nucleic acid | complementary strand |
| enzyme substrate | enzyme |
| DNA (RNA) | cDNA (cRNA)† |
| hormone | hormone receptor |
| ion | chelator |

*IgG is an immunoglobulin
†cDNA and cRNA are complementary strands used for hybridization Alternatively, a monomer, labeled with a quenching compound, is incorporated into a polymer labeled with a luminophore, resulting in quenching of luminescence. In particular, a quenching compound-labeled nucleotide can be incorporated via the polymerase chain reaction into a double stranded DNA molecular that is labeled with a luminophore.

Detection of Structural Disassembly

In another embodiment of the method of the invention, the disassembly, cleavage or other degradation of a molecular structure is detected by observing the partial or complete restoration of luminescence of a luminophore donor. Typically, the initially quenched luminescence of a luminophore associated with the structure becomes dequenched upon being released from the constraint of being in close proximity to a quenching compound of the invention. The quenching compound is optionally associated with the same molecular structure as the luminophore, or the donor and acceptor are associated with adjacent but distinct subunits of the structure. The following systems, among others, can be analyzed using energy transfer pairs to detect and/or quantify structural disassembly:

detection of protease activity using fluorogenic substrates (for example HIV protease assays)
detection of enzyme-mediated protein modification (e.g. cleavage of carbohydrates/fatty acids, phosphates, prosthetic groups)
immunoassays (via displacement/competitive assays)
detection of DNA duplex unwinding (e.g. helicase/topoisomerase/gyrase assays)
nucleic acid strand displacement
ds DNA melting
nuclease activity
lipid distribution and transport
TAQMAN assays Structure disassembly is typically detected by observing the partial or complete restoration of luminescence, as a conjugated substance is exposed to a degradation conditions of interest for a period of time sufficient for degradation to occur. A restoration of luminescence indicates an increase in separation distance between the luminophore and quenching compound, and therefore a degradation of the conjugated substance. If the detectable difference in luminescence is detected as the degradation proceeds, the assay is a continuous assay. Since most enzymes show some selectivity among substrates, and as that selectivity can be demonstrated by determining the kinetic differences in their hydrolytic rates, rapid testing for the presence and activity of the target enzyme is provided by the enhancement of luminescence of the labeled substrate following separation from the quenching compound.

In another embodiment of the invention, a single-stranded oligonucleotide signal primer is labeled with both a quenching compound and a fluorescent donor dye, and incorporates a restriction endonuclease recognition site located between the donor dye and the quenching compound. The single-stranded oligonucleotide is not cleavable by a restriction endonuclease enzyme, but upon binding to a complementary (target) nucleic acid, the resulting double stranded nucleic acid is cleaved by the enzyme and the decreased quenching is used to detect the presence of the complementary nucleic acid (U.S. Pat. No. 5,846,726 to Nadeau et al., (1998)).

In yet another embodiment of the invention, structural disassembly can be detected by the quenching of luminescence. In this embodiment, the action of an oxidative enzyme on a colorless precursor results in the generation of a quenching compound of the invention. The newly generated quenching compound then quenches the luminescence of a luminophore if it is in sufficiently close proximity, indicating the presence and/or activity of the enzyme.

Alternatively, where $R^7$ is selected so as to make the colorless precursor an enzyme substrate (where $R^7$ is a monovalent radical formally derived by removing a hydroxy group from a carboxylic acid, a sulfonic acid, a phosphoric acid, or a mono- or polysaccharide), the generation of the quenching compounds of the invention indicates the presence of the particular enzyme. In another embodiment, $R^7$ is a photolabile caging group, including but not limited to o-nitroarylmethine derivatives, 2-methoxy-5-nitrophenyl derivatives, or desyl derivatives.

A single nucleotide polymorphism (SNP) can be detected through the use of sequence specific primers, by detection of melt temperatures of the double stranded nucleic acid. In this aspect, the complementary or substantially complementary strands are labeled with a quenching compound and a luminophore donor, respectively, and dissociation of the two strands (melting) is detected by the restoration of luminescence of the donor.

In yet another example of a divergence assay, the rupture of a vesicle containing a highly concentrated solution of luminophores and quenching compounds is readily detected by the restoration of luminescence after the vesicle contents have been diluted sufficiently to minimize quenching.

Detection of conformation changes

In this embodiment, the quenching compound and the fluorescent donor are present on the same or different substances, and a change in the three-dimensional structural conformation of one or more components of the assay results in either luminescence quenching or restoration of luminescence, typically by substantially decreasing or increasing the separation distance between the quenching compound and a luminophore. The following systems, among others, can be analyzed using energy transfer pairs to detect and/or quantify conformation changes:

protein conformational changes
protein folding
structure and conformation of nucleic acids
drug delivery
antisense oligonucleotides
cell-cell fusion (e.g. via the diffusion apart of an initial donor-quenching compound pair)

By conformation change is meant, for example, a change in conformation for an oligonucleotide upon binding to a complementary nucleic acid strand. In one such assay, labeled oligonucleotides are substantially quenched when in solution, but upon binding to a complementary strand of nucleic acid become highly fluorescent (so-called "Molecular Beacons", as described in European patent application EP 0 745 690, by Tyagi et al (1996)). Another example detects the change in conformation when an oligonucleotide that has been labeled at its ends with a quenching compound and a luminophore, respectively, loses its G-quartet conformation upon hybridization to a complementary sequence, resulting in decreased luminescence quenching (U.S. Pat. No. 5,691,145 to Pitner et al. (1997)). Alternatively, the binding of an enzyme substrate within the active site of a labeled enzyme may result in a change in tertiary or quaternary structure of the enzyme, with restoration or quenching of luminescence.

Additional Detection Reagents

When used in complex systems, especially in biological cells, the assays of the instant invention are optionally combined with the use of one or more additional detection reagents, such as an antibody, or a stain for another component of the system such as a nucleic acid stain, an organelle stain, a metal ion indicator, or a probe to assess viability of the cell. The additional detection reagent is optionally a fluorescent reagent exhibiting a color that contrasts with the donor dye present in the assay, or is a label that is detectable by other optical or non-optical properties.

Kits

One aspect of the instant invention is the formulation of kits that facilitate the practice of the methods of the invention, as described above. The kit of the invention comprises a quenching compound of the invention, or colorless quenching compound precursor of the invention, typically present conjugated to a nucleotide, oligonucleotide, nucleic acid polymer, peptide, or protein. Typically, the kit further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

In one embodiment, the kit comprises a quenching compound of the invention and a luminescent donor. The quenching compound and luminescent donor are optionally each attached to a conjugated substance, or present in solution as free compounds. Such a kit would be useful for the detection of cell-cell fusion, as fusion of a cell containing the quenching compound with a cell containing a luminescent donor would result in quenching of luminescence. Conjugation of either the quenching compound or the luminescent donor or both to biomolecules, such as polysaccharides, would help retain the reagents in their respective cells until cell fusion occurred.

In another embodiment, the kit comprises a quenching compound and a luminescent donor, each conjugated to a complementary member of a specific binding pair. In this aspect of the invention, binding of the two specific binding pair members results in quenching of luminescence, and the kit is useful for the detection of competitive binding to one or the other specific binding pair members, or for the detection of an environmental condition or component that either facilitates or inhibits binding of the specific binding pair members.

In another embodiment, the kit comprises a conjugate of a quenching compound and a conjugate of a luminescent donor, wherein the conjugates are selected such that the action of a particular enzyme results in covalent or noncovalent association of the two conjugates, resulting in quenching of fluorescence. Where the conjugated substances are nucleotides, oligonucleotides or nucleic acid polymers, the kit is useful for the detection of, for example, ligase, telomerase, helicase, topoisomerase, gyrase, DNA/RNA polymerase, or reverse transcriptase enzymes.

In another embodiment, the kit comprises a biomolecule that is covalently labeled by both a quenching compound of the invention and a luminescent donor. In one aspect, the labeled biomolecule exhibits luminescence until a specified environmental condition (such as the presence of a complementary specific binding pair) causes a conformation change in the biomolecule, resulting in the quenching of luminescence. Alternatively, the biomolecule is initially quenched, and a specified environmental condition (such as the presence of an appropriate enzyme or chemical compound) results in degradation of the biomolecule and restoration of luminescence. Such a kit would be useful for the detection of complementary oligonucleotide sequences (as for MOLECULAR BEACONS™, supra), or for the detection of enzymes such as nuclease, lipase, protease, or cellulase.

Synthesis

Rhodamine dyes are typically prepared by condensation of an appropriate aminophenol with various derivatives of benzoic acid, phthalic acid or phthalic anhydride or sulfobenzoic acid or its anhydride. In the case of the quenching compounds of the invention, the aminophenol is typically an N-aryl or N-heteroaryl substituted aminophenol. Useful derivatives of benzoic acid include, without limitation, phthalic anhydride, trimellitic anhydride, nitrophthalic anhydride, polyhalogenated phthalic anhydrides, o-sulfobenzoic anhydride, sulfoterephthalic acid, or benzaldehydes or aliphatic dicarboxylic acids or anhydrides such as a succinic anhydride or a glutaric anhydride. This condensation reaction occurs in the presence or absence of various acid catalysts (such as zinc chloride, p-toluenesulfonic acid, sulfuric acid, or methanesulfonic acid). An aqueous workup, typically followed by column chromatography, yields the desired xanthylium dye.

If an unsymmetric rhodamine dyes is desired, the condensation can be performed using one equivalent each of the appropriate substituted or unsubstituted aminophenol with one equivalent of a different aminophenol and with one equivalent of the appropriate phthalic acid derivative or benzaldehyde (as listed above) using acid catalysis (as in Khanna et al., U.S. Pat. No. 4,439,359 (1984) and Haugland et al., U.S. Pat. No. 5,227,487 (1993)). The desired asymmetric rhodamine dye is separated from any unwanted symmetric dye side-product(s) using crystallization or chromatographic techniques well-known in the art.

Unsymmetric rhodamine dyes can also be constructed in a stepwise fashion: A selected aminophenol is condensed with one equivalent of the appropriate benzoic or phthalic acid derivative or benzaldehyde. The resulting benzophenone derivative is typically isolated, purified and then condensed with one equivalent of a different aminophenol, yielding the asymmetric dye.

Rhodol dyes are prepared by condensation of one equivalent each of the appropriate substituted or unsubstituted resorcinol with one equivalent of the desired N-aryl or N-heteroaryl aminophenol and with one equivalent of the appropriate phthalic acid derivative or benzaldehyde using acid catalysis (U.S. Pat. No. 5,227,487 to Haugland et al. (1993), incorporated by reference). Appropriate phthalic acid derivatives and benzaldehydes include but are not limited to phthalic anhydride, trimellitic anhydride, nitrophthalic anhydride, tetrafluorophthalic anhydride, sulfoterephthalic acid, succinic anhydride, or their corresponding phthalic acids or pentafluorobenzaldehyde. The desired rhodol dye is separated from any unwanted symmetrical dye side-product using chromatographic techniques well-known in the art.

Aryl and heteroaryl substituted xanthylium dyes are also readily prepared by displacement of the chloro groups from 3,6-dichlorofluoran or 3,6-dichlorosulfonefluoran using an appropriately substituted amine (Equation 1; U.S Pat. No. 4,258,118 and German Patent 24 60 491). 5-Carboxy-3,6-dichlorosulfonefluoran is readily converted to a 5-carboxy-3,6-diarylamino derivative using a similar methodology.

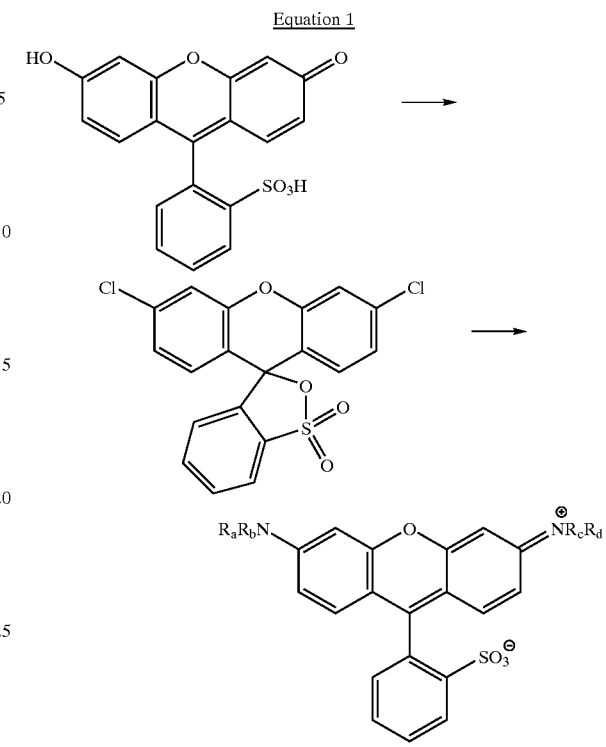

Equation 1

A variety of aryl-substituted rhodamines may be prepared using this method (Example 1).

The post-condensation modification of rhodamine and rhodol dyes is well known in the chemical arts. For example, the xanthenone portion of the dye can be halogenated by treatment with the appropriate halogenating agent, such as liquid bromine. Xanthenes containing unsaturated fused rings can be hydrogenated to the saturated derivatives. The Q moieties are also subject to synthetic modification, either after the condensation reaction, or by modification of aryl and heteroaryl moieties on synthetic precursors.

When trimellitic anhydride or its derivatives is used in the dye synthesis, two isomeric carboxylates are typically formed. These isomers are separated or, in most cases, used as the mixture of isomers. The reduced derivatives of xanthylium dyes are prepared by chemical or electrochemical reduction of the xanthenone portion, such as with zinc dust or borohydride in organic solvents. Sulfonation of xanthylium dyes on the xanthene ring is typically carried out by stirring the dye in fuming sulfuric acid (20–30% $SO_3$ content) or concentrated sulfuric acid at an appropriate temperature. In some cases, sulfonation on aryl or heteroaryl moieties is possible under these conditions.

The selection of an appropriate polyhalogenated phthalic acid derivative or benzaldehyde in the condensation of the xanthylium dye results in a dye having a di-, tri-, tetra- or pentachlorinated or di-, tri-, tetra- or pentafluorinated phenyl ring at the 9-position. Some of these polyhaloaryl substituted dyes have been shown to react with thiols via a displacement reaction, and thereby provide a facile method of introducing additional reactive groups (Gee, et al. TET. LETT. 37, 7905 (1996)).

The reduced (e.g. dihydrorhodamine) and oxidized versions of the dyes of the invention are freely interconvertible by well-known oxidation or reduction reagents, including borohydrides, aluminum hydrides, hydrogen/catalyst, and dithionites. A variety of oxidizing agents mediate the oxidation of dihydrorhodamines, including molecular oxygen in the presence or absence of a catalyst, nitric oxide, peroxynitrite, dichromate, triphenylcarbenium and chloranil. The dihydrorhodamines are also oxidized by enzyme action, including horseradish peroxidase in combination with peroxides or by nitric oxide.

In general, the preparation of dye conjugates using reactive dyes is well documented, e.g. by R. Haugland, MOLECULAR PROBES HANDBOOK OF FLUORESCENT PROBES AND RESEARCH CHEMICALS, Chapters 1–3 (1996); Brinkley, BIOCONJUGATE CHEM., 3, 2 (1992); Haugland, "Coupling of Monoclonal Antibodies with Fluorophores", METH. MOL. BIOL. Vol. 45, 205). Conjugates typically result from mixing appropriate reactive dyes and the substance to be conjugated in a suitable solvent in which both are soluble. For those reactive dyes that are photoactivated, conjugation requires illumination of the reaction mixture to activate the reactive dye.

By selection of the appropriate reactive functional group, substances having free amine, thiol, aldehyde or ketone groups are readily coupled to the quenching compounds of the invention by means well known in the art, as described below:

A 5–40 fold molar excess of a succinimidyl ester derivative (such as Compound 5, 8, 11, 13, 24, or 26) may be coupled to an aliphatic amine-modified nucleotide or oligonucleotide in a pH 8.3 buffer (borate or bicarbonate buffer) for greater than 1 hour. The products are purified by HPLC and characterized by their absorption spectra. Succinimidyl ester derivatives may also be coupled to amine-containing peptides or proteins, or to amino saccharides or polysaccharides in a suitable buffer such as borate or bicarbonate buffer and purified either by HPLC or size exclusion chromatography. Conjugates are characterized for their degree of substitution by spectroscopic methods.

Thiolated biomolecules are typically conjugated to thiol-reactive dyes such as Compound 22 at a pH less than 8. Aldehyde- or ketone-containing molecules are typically modified by an amine-, hydrazine- or hydroxylamine-containing dye of the invention (for example Compounds 21 and 30), sometimes followed by chemical reduction of the resulting imine, such as by a borohydride. Low molecular weight molecules are typically prepared in an organic solvent or water, purified chromatographically and characterized for purity by HPLC.

Oligonucleotides conjugated to both a donor dye and a quenching acceptor are readily prepared, preferably by some combination of amine-reactive, thiol-reactive or phosphoramidite derivatives (such as Compound 3). Typically one of the conjugated dyes is a quenching compound of the invention, and at least one of the other conjugated dyes is intrinsically fluorescent Peptides for use, in particular, as endoprotease substrates that comprise both a fluorescent donor dye and a quenching compound of the invention are synthesized either by modification of peptides that have suitable reactive sites or by use of a building block such as the quenching compound-lysine conjugate (Compound 25).

The examples below are given so as to illustrate the practice of this invention. They are not intended to limit or define the entire scope of this invention.

EXAMPLES

Example 1

Preparation of Aryl-substituted Rhodamine Sulfonic Acid Compounds

Aryl and heteroaryl substituted xanthylium dyes are readily prepared by displacement of the chloro groups from a 3,6-dichlorofluoran or a 3,6-dichlorosulfofluoran using the desired substituted amine (U.S Pat. No. 4,258,118 and German Patent 24 60 491) as shown in Table 2.

TABLE 2

| AMINE USED | RESULTING PRODUCT |
|---|---|
| (aniline, NH₂) | (N-methylaniline, CH₃-NH) |
| (N-methylaniline, CH₃-NH) | Compound B |

TABLE 2-continued
| AMINE USED | RESULTING PRODUCT |
|---|---|
|  | 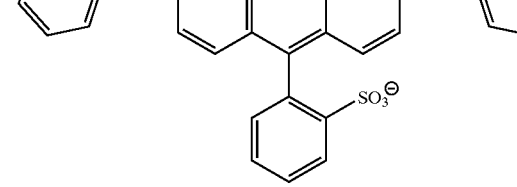
Compound C |
|  | 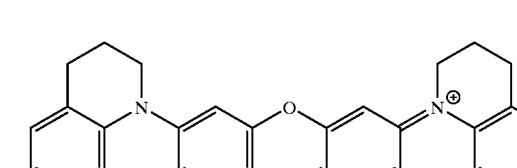
Compound D |
|  | 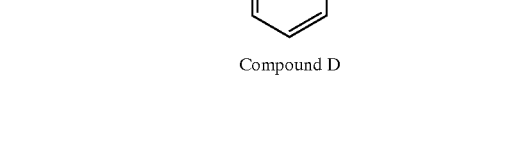
Compound E |
|  | 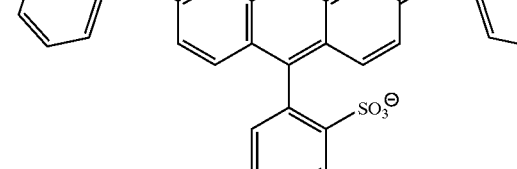
Compound F |

TABLE 2-continued

| AMINE USED | RESULTING PRODUCT |
|---|---|
| 4-methoxy-N-methylaniline | Compound G |
| 2-aminopyridine | Compound H |
| 2-aminobenzothiazole | Compound I |
| 2-aminothiazole | Compound J |
| 4-aminobenzenesulfonate | Compound K |

TABLE 2-continued

| AMINE USED | RESULTING PRODUCT |
|---|---|
| (aniline, PhNH$_2$) | Compound L |

TABLE 3

| Compound | Absorbance $\lambda_{max}$ (nm) | Quantum Yield |
|---|---|---|
| A | 553 | nd |
| B | 555 | nd |
| C | 615 | nd |
| D | 629 | nd |
| E | 634 | nd |
| F | nd | nd |
| G | 556 | nd |
| H | 548 | ~0.009 |
| I | 574 | ~0.006 |
| J | 528 | nd |
| 5 | 561 | ~0.0009 |
| 8 | 660 | ~0.0002 |
| 10 | 558 | ~0.001 |
| 13 | 560 | ~0.002 |
| 16 | 649 | ~0.0001 |
| 27 | 553 | ~0.002 |
| 28 | 560 | ~0.0002 | nd = not determined

Example 2

Preparation of a Phosnhoramidite Derivative (3)

Compound B of Example 1 (2 g) is heated in 20 mL of phosphorous oxychloride at 70° C. for 6 hours. The solution is evaporated under reduced pressure and the residue is dried in vacuo for several hours to yield the sulfonyl chloride derivative (Compound 1).

Compound 1

The crude sulfonyl chloride thus generated is stirred in 45 mL of acetonitrile and cooled to 0° C. To this cold solution is added a mixture of 1.2 g of 3-piperidinemethanol, 2 mL of triethylamine in 6 mL of DMF and 10 mL of acetonitrile. After one hour the acetonitrile is evaporated, the reaction mixture is poured into 1 M HCl and extracted with chloroform. Following evaporation, the crude residue is purified on a silica gel column to yield 1.7 g of the methanol adduct 2:

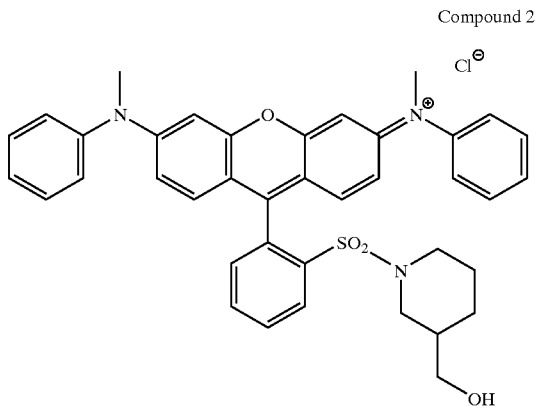

Compound 2

To 136 mg of 2 in 2 mL of methylene chloride at 0° C. under nitrogen is added sequentially 0.19 mL of diisopropylethylamine and 0.23 mL of 2-cyanoethyl diisopropyl-chlorophosphoramidite. The reaction mixture is stirred for 5 minutes then poured onto sodium bicarbonate and extracted with methylene chloride. The methylene chloride is removed under reduced pressure to yield the phosphoramidite derivative, 3.

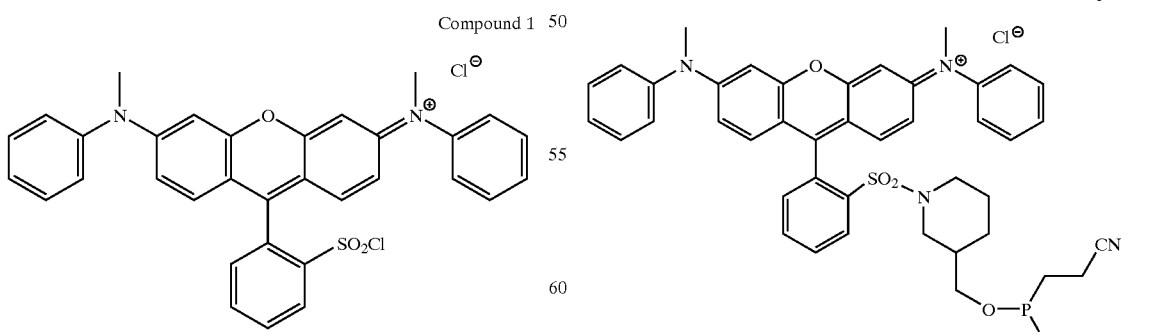

Compound 3

The phosphoramidite derivative is useful for the preparation of quenching compound-labeled oligonucleotides using an automated synthesizer.

Example 3

Preparation of a Succinimidyl Ester Derivative (5)

Isonipecotic acid (20.5 g) is heated at reflux for 30 minutes in 80 mL of hexamethyldisilazane in the presence of a catalytic amount of concentrated sulfuric acid. Excess hexamethyldisilazane is evaporated and the residue is dissolved in 150 mL of acetonitrile and cooled to 0–5° C. Triethylamine (23 mL) is added, followed by 29 g of the sulfonyl chloride derivative Compound 1 in 150 mL of acetonitrile to generate Compound 4, which is isolated by evaporation of the solvent, addition of 1 M HCl, extraction into chloroform and evaporation.

Compound 4

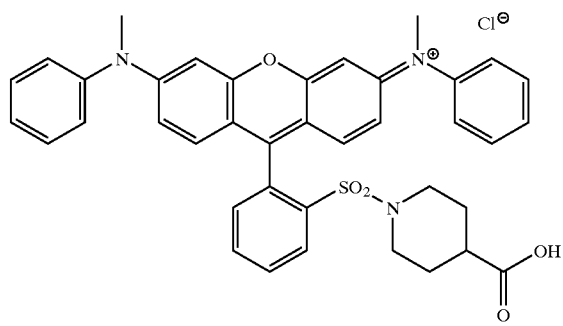

To a stirring solution of Compound 4 (2.26 g) in 20 mL of acetonitrile at room temperature are added sequentially 1.1 mL of diisopropylethylamine and 1.7 g of 2-succinimido-1,1,3,3-tetramethyluronium tetrafluoroborate. The resulting mixture is stirred at room temperature for one hour. The solution is partitioned between CHCl$_3$ and 1 M HCl, and the organic portion is evaporated and recrystallized from CH$_3$CN and diethyl ether to yield the desired succinimidyl ester, Compound 5.

Compound 5

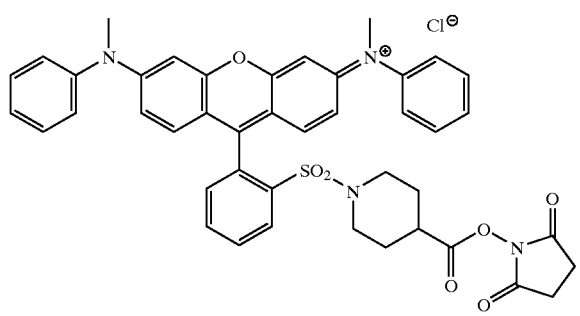

Example 4

Preparation of a Succinimidyl Ester Derivative (8)

A mixture of 2 g of Compound C (Example 1) and 20 mL of phosphorous oxychloride is heated at 65° C. for 6 hours. Excess reagents are removed under vacuum and the residue is dissolved in 50 mL of acetonitrile and cooled to ca. 10° C. To this solution is added 9.2 mL of diisopropylethylamine and 10.8 mL of ethyl isonipecotate. After 2 hours the acetonitrile is removed under vacuum and the reaction is worked up with 1 M HCl and extracted into chloroform. The crude product is purified on a silica gel column to yield 1.88 g of the pure ester 6.

Compound 6

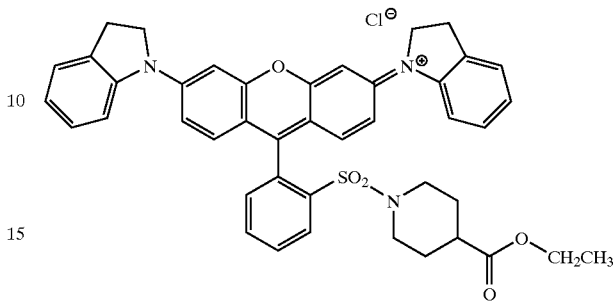

To 0.31 g of ester 6 in 60 mL of methanol is added 1.5 mL of a 10% NaOH solution and the mixture is heated at 35–40° C. overnight. Another 2 mL of 10% NaOH is introduced and heating is continued for another 20 hours. The reaction mixture is cooled to room temperature, 120 mL of 1 M HCl is added and after another hour the product is filtered to give product 7.

Compound 7

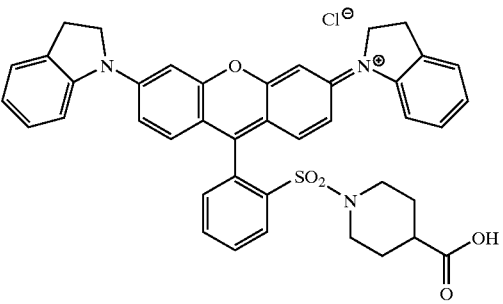

To 98 mg of acid 7 in 1.5 mL of DMF is added 0.07 mL of diisopropylethylamine and 66 mg of 2-succinimido-1,1,3,3-tetramethyluronium tetrafluoroborate. The reaction is worked up with chloroform and 1 M HCl and the organic extracts are dried over magnesium sulfate. The crude material is dissolved in 2 mL of acetonitrile. Ethyl acetate (8 mL) is added dropwise and after stirring overnight the solution is filtered to yield 80 mg of product 8.

Compound 8

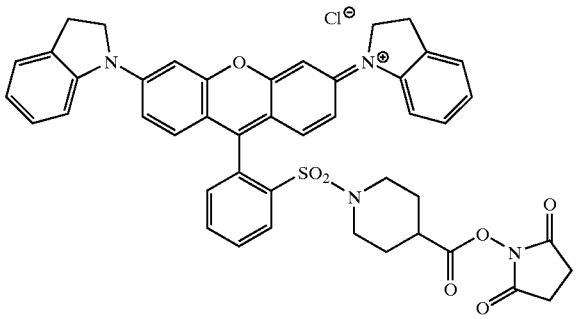

Example 5

Preparation of a Succinimidyl Ester Derivative (11)

A mixture of 5.52 g of 3-hydroxydiphenylamine, 2.21 g of phthalic anhydride, and 2.04 g of $ZnCl_2$ is heated at 180° C. for 1.5 hour. A mixture of methanol (150 mL) and water (50 mL) is added and the mixture is heated at reflux overnight. The solid is filtered and then refluxed again in 100 mL of methanol and 50 mL of water for 3 hours. The mixture is filtered to yield the acid 9.

Compound 9

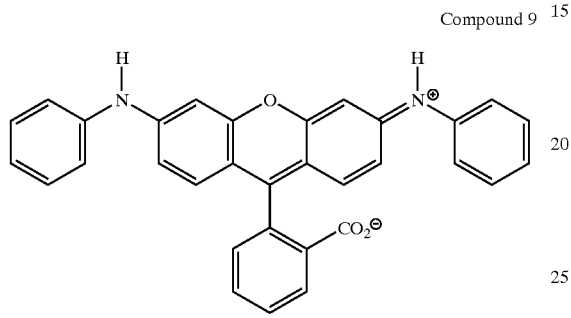

The carboxylic acid 9 (1.5 g) is heated at 70–75° C. in 15 mL of phosphorous oxychloride overnight to generate the acid chloride. Volatiles are removed under reduced pressure. The residue is dissolved in 30 mL of DMF followed by the addition of 2.4 mL of triethylamine and 2.37 g of ethyl isonipecotate. After several hours at room temperature, the DMF is removed and the residue is dissolved in 30 mL of chloroform and chromatographed on silica gel to yield 0.65 g of the ethyl ester 10.

Compound 10

The ethyl ester 10 is hydrolyzed by stirring in 15 mL of methanol and 2 mL of 10% NaOH at 35° C. for 2 hours. HCl (60 mL of 1 M) is added dropwise and the mixture is filtered to yield 0.61 g of the crude acid. 65 mg of this acid is converted to its succinimidyl ester by stirring with 0.147 g of 1-[3-(dimethylamino)propyl]-3-ethylcarbodiimide hydrochloride, 89 mg of N-hydroxysuccinimide, and 0.2 mL of pyridine in 2 mL of DMF at room temperature for 20 hours. The mixture is then added to 50 mL of cold 1 M HCl and filtered to yield 58 mg of product 11.

Compound 11

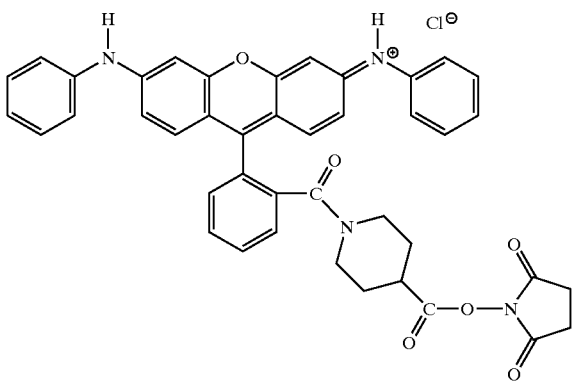

Example 6

Preparation of a Succinimidyl Ester (13)

To acid 4 (Example 2, 1.5 g) in 20 mL of methylene chloride is added 0.72 mL of chlorosulfonic acid, followed by 4.5 mL of acetic anhydride. The mixture is stirred at room temperature overnight and 100 mL of ether is added precipitate the crude product. Purification is by chromatography on a silica gel column eluting with 9:1 acetonitrile/water to yield 1.0 g of the pure sulfonated derivative 12.

Compound 12

To 0.6 g of acid 12 in 60 mL of DMF at room temperature is added 0.48 mL of diisopropylethylamine and 0.93 g of 2-succinimido-1,1,3,3-tetramethyluronium tetrafluoroborate. The mixture is stirred for 30 minutes. Ethyl acetate (240 mL) is added. The mixture is stirred overnight and the product 13 is recovered by filtration.

Compound 13

Example 7

Preparation of a Succinimidyl Ester Derivative (15)

To 0.2 g of ester 6 in 5 mL of methylene chloride is added 1 mL of acetic anhydride and 71 µL of chlorosulfonic acid. After stirring overnight at room temperature, ethyl acetate (15 mL) is added dropwise and product 14 is recovered by filtration.

Compound 14

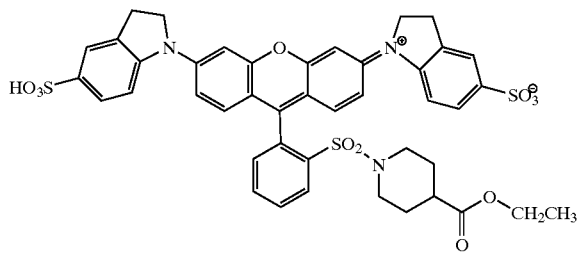

Ester 14 (100 mg) is hydrolyzed by stirring in 25 mL of methanol and 2 mL of 10% NaOH at 35° C. overnight. HCl (10 mL of 1 M) is added, the volume is reduced to 5 mL and then filtered to yield the acid 15.

Compound 15

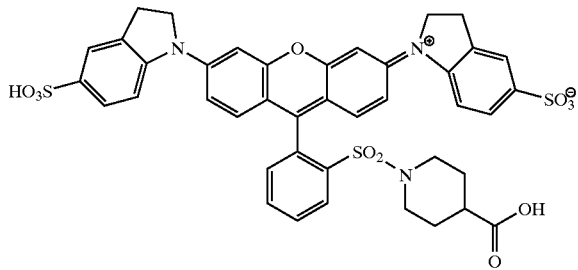

Diisopropylethylamine (34 µL) and 30 mg of 2-succinimido-1,1,3,3-tetramethyluronium tetrafluoroborate are added to 44 mg of acid 15 in 2 mL of DMF. After 15 minutes at room temperature, ethyl acetate (4 mL) is added and the mixture is filtered to yield the crude product. This is stirred in 5 mL of acetonitrile for 30 minutes and filtered again to yield the ester 16.

Compound 16

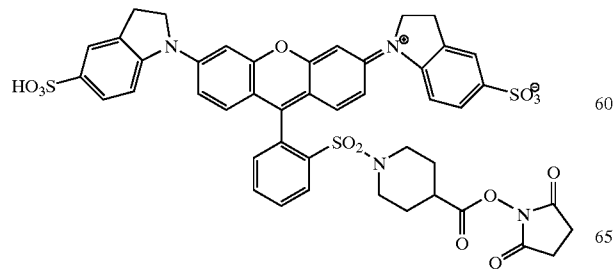

Example 8

Preparation of an Acid Derivative (18)

A mixture of 0.83 g of 5-carboxysulfonefluorescein (prepared according to methods provided in International Publication WO 97/39064 (1997)), 1.26 g of phosphorus pentachloride, and 2.5 mL of phosphorus oxychloride is heated at 130° C. for 2 hours. The mixture is cooled and poured onto 80 mL of cold water and stirred for one hour. The solid is filtered and stirred in 20 mL of 5% NaOH for 30 minutes. The solution is acidified with 20 mL of 6 M HCl. The crude 5-carboxy-3,6-dichlorosulfonefluoran is filtered and purified by stirring it in 50 mL of methanol for several hours to yield 0.13 g of the dichlorosulfonefluorancarboxylic acid 17.

Compound 17

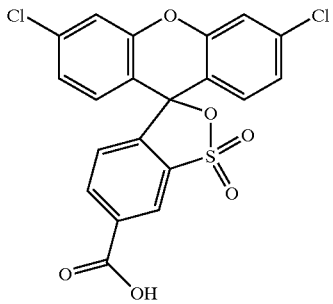

The fluoran 17 (50 mg) is heated with 1 mL of N-methylaniline at 70° C. for 3 hours. Volatile components are removed at 40° C. in vacuo. The residue is dissolved in chloroform and washed with 1 M HCl to yield the crude material, which is purified by recrystallization from chloroform/ethyl acetate to yield 35 mg of the pure acid 18.

Compound 18

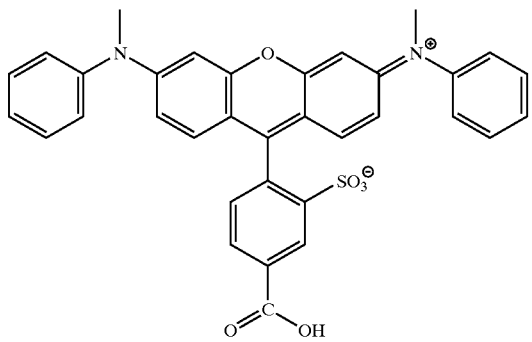

Example 9

Preparation of an Alcohol Derivative (20)

Compound C of Example 1 (0.42 g) is heated at 70° C. for 4 hours in 4 mL of phosphorous oxychloride. The reaction mixture is evaporated in vacuo to yield the crude sulfonyl chloride 19.

Compound 19

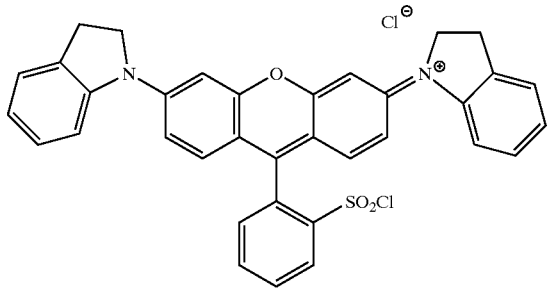

To a solution of the crude sulfonyl chloride 19 in 10 mL of acetonitrile at 0° C. is added dropwise a mixture of 0.25 g of 3-piperidinemethanol, 0.4 mL of triethylamine in 2 mL of DMF and 3 mL of acetonitrile. After 1 hour the reaction is worked up with 1 M HCl and chloroform and purified on a silica gel column to yield 0.3 g of product 20.

Compound 20

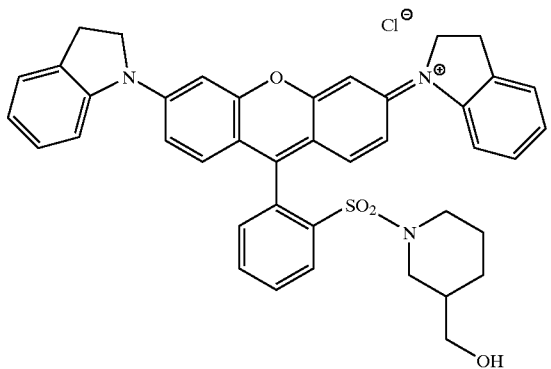

Example 10

Preparation of a Cadaverine Derivative (21)

A mixture of 0.5 g of the succinimidyl ester Compound 5 (Example 3), 0.153 g of mono-N-(t-BOC)-cadaverine and 0.17 mL of diisopropylethylamine in 15 mL of methylene chloride is stirred at room temperature overnight. The reaction mixture is worked up with 1 M HCl and purified on a silica gel column to yield 0.31 g of the pure t-BOC protected sulfonamide. This product is deprotected by dissolving it in 15 mL of methylene chloride and stirring overnight with 0.5 mL of 4 M HCl in dioxane at room temperature. Following removal of volatiles under reduced pressure, the residue is stirred in 20 mL of ether to yield 0.29 g of the amine 21 as the hydrochloride salt.

Compound 21

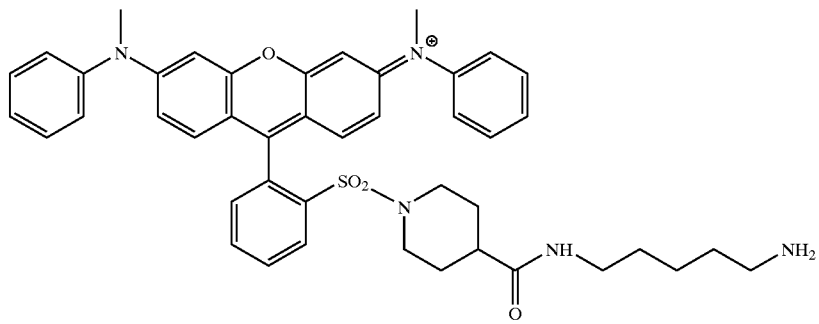

Example 11

Preparation of a Maleimide Derivative (22)

To the succinimidyl ester Compound 5 of Example 3 (0.5 g) in 15 mL of methylene chloride at room temperature is added 0.23 mL of diisopropylethylamine, followed by 0.26 g of N-(5-aminopentyl)maleimide trifluoroacetic acid salt. The solution is stirred at room temperature for 3 hours and is then worked up with 1 M HCl. The crude maleimide is purified on a silica gel column to yield 0.35 g of pure product 22.

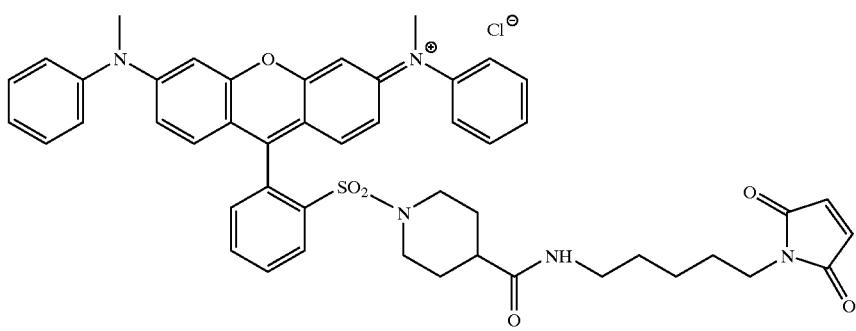

Compound 22

Example 12

Preparation of a Succinimidyl Ester Derivative (24)

Compound A of Example 1 (0.375 g) is heated with 5 mL of phosphorous oxychloride at 60–65° C. for 4 hours. Excess reagent is removed under reduced pressure and to the crude sulfonyl chloride is added 40 mL of acetonitrile, followed by addition of a mixture of 2.3 g of ethyl isonipecotate and 2.42 mL of triethylamine in 10 mL of acetonitrile. After stirring at room temperature for one hour, volatiles are removed by evaporation under reduced pressure. To the residue is added 60 mL of methanol followed by 20 mL of 10% NaOH. The mixture is heated at 50° C. for one hour. The volume is reduced to about 1/3 and 90 mL of 2 M HCl is added at 0° C. The solid is collected by filtration and dried in vacuo to yield 0.43 g of the crude nipecotic acid derivative 23.

Compound 23

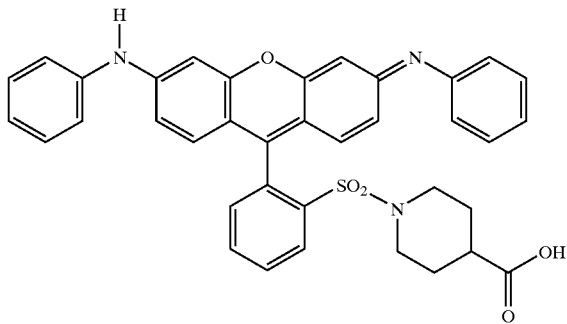

To 100 mg of acid 23 in 6 mL of DMF and 0.2 mL of pyridine is added 192 mg of 1-[3-(dimethylamino)propyl]-3-ethylcarbodiimide hydrochloride and 115 mg of N-hydroxysuccinimide. After stirring overnight at room temperature, the DMF solution is added to 100 mL of cold 1 M HCl and filtered to yield the succinimidyl ester 24.

Compound 24

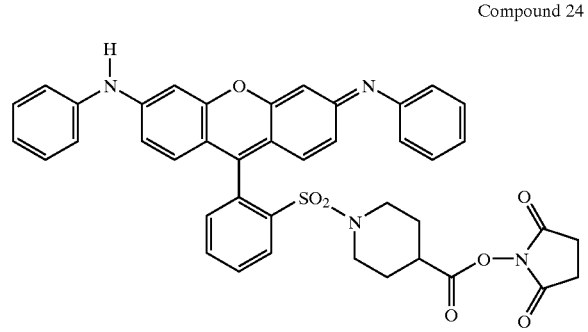

Example 13

Preparation of a Lysine Derivative (25)

To 0.41 g of Compound 24 in 10 mL of DMF and 3 mL of pyridine at room temperature is added 0.57 g of α-FMOC-L-lysine hydrochloride. The mixture is stirred at room temperature for three days, followed by warming at 35° C. for 30 minutes. The solution is poured into 130 mL of cold 1 M HCl. The crude residue is filtered and dried in vacuo then purified on a silica gel column to yield 0.55 g of the α-FMOC-L-lysine 25.

Compound 25

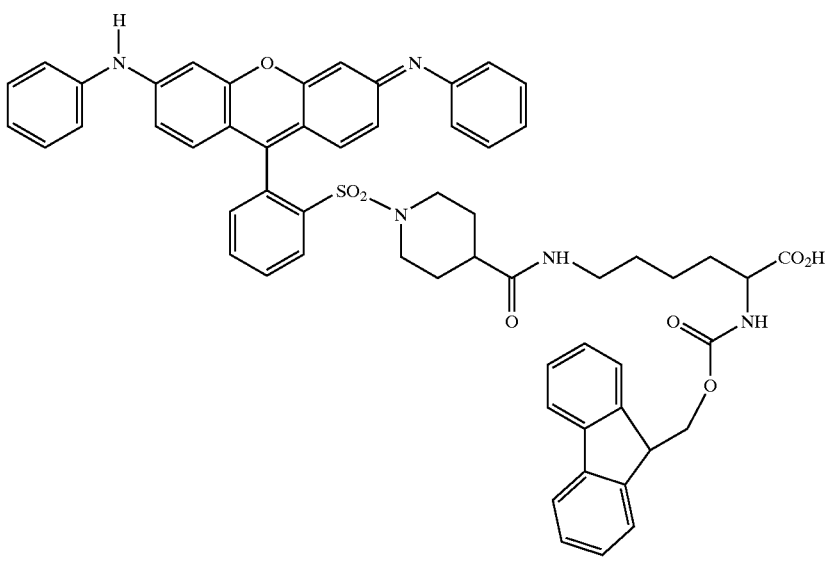

Example 14

Preparation of a Succinimidyl Ester Derivative (26)

To Compound E (Example 1) is added 2.2 equivalents of ethyldiisopropylamine, followed by 2.4 equivalents of 2-succinimido-1,1,3,3-tetramethyluronium tetrafluoroborate. The reaction mixture is stirred for 20 minutes. Three volumes of ethyl acetate are added to the reaction mixture dropwise, and the resulting solid is collected to obtain the succinimidyl ester 26.

Compound 26

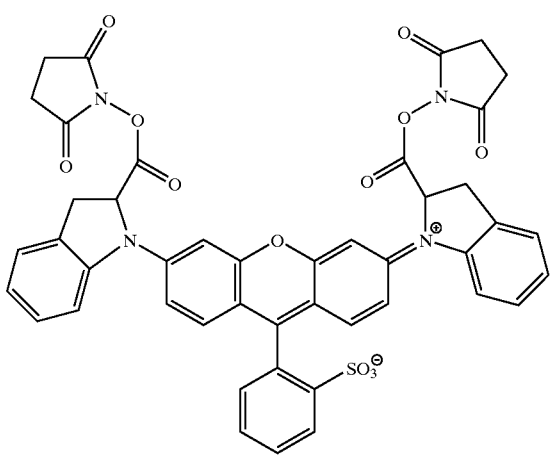

Example 16

Preparation of a Hydroxyl Derivative (27)

A mixture of 0.75 g of Compound 9 (Example 11) and 7.5 mL of phosphorous oxychloride is heated at 60° C. overnight to generate the corresponding acid chloride. Excess oxychloride is evaporated and the resulting residue is dried under vacuum at 40° C. for 2 hours. The crude material is then dissolved in a solution of 30 mL of acetonitrile and 3 mL of DMF at room temperature. To this solution is added a mixture of 1.1 g of 6-methylaminohexanol and 1.2 mL of triethylamine in 5 mL of acetonitrile. After the reaction mixture is stirred at room temperature for 2 hours, all volatile components are removed under reduced pressure. The resulting residue is partitioned between chloroform and 1 M HCl, and the organic layer is dried and subjected to silica gel chromatography to yield Compound 27.

Compound 27

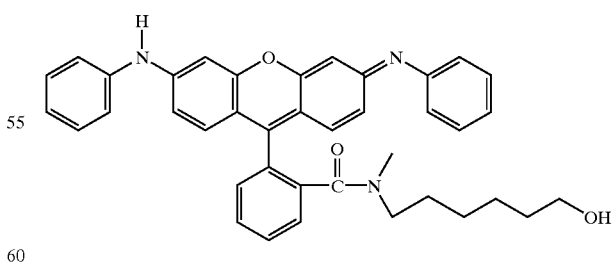

Example 17

Preparation of a Hydroxy Derivative (28)

Compound 28 is prepared analogously to the method provided for Compound 27 (Example 16), except that Compound A of Example 1 is used instead of Compound 9.

Compound 28

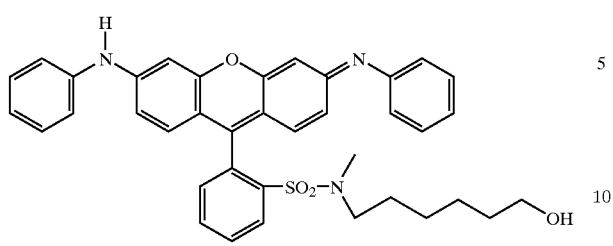

Example 18

Preparation of a Biotinylated Derivative (29)

To 25 mg of Compound 5 (Example 3) in 1 mL of DMF is added 17 mg of N-(5-aminopentyl)biotinamide trifluoroacetic acid salt and 6 μL of triethylamine. After the reaction mixture is stirred for 2 hours, 6 mL of a 1/1 (v/v) brine and water solution is added dropwise, and the resulting sticky crude material is purified on a silica gel chromatography column to yield Compound 29.

Example 19

Preparation of a Hydrazine Derivative (30)

Compound 5 (example 3) is treated with a molar excess of hydrazine hydrate in methanol solution. After reaction is complete, the desired product is precipitated by the addition of water, the solid is collected, and purified by silica gel chromatography to yield Compound 30.

Compound 30

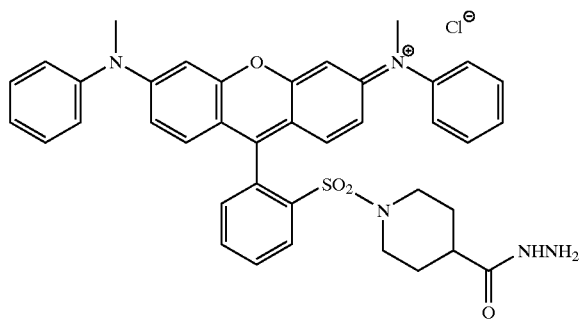

Compound 29

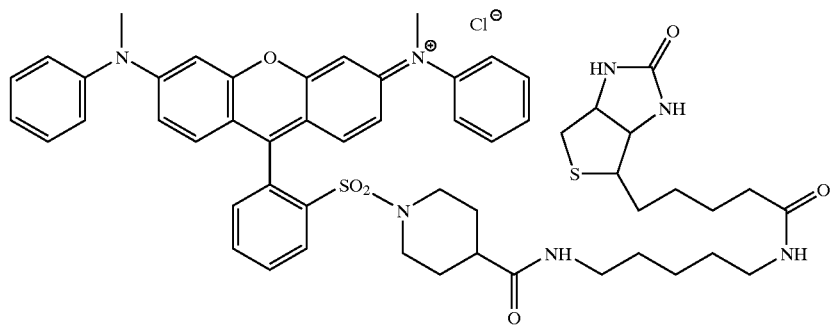

Example 20

Preparation of a Phospholipid Derivative (31)

Compound 31

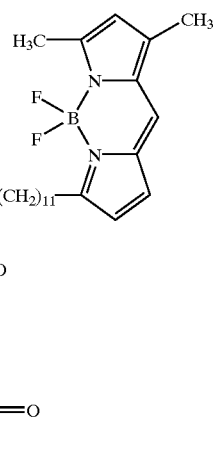

To a solution of 2.5 mg (0.003 mmol) of 2-(4,4-difluoro-5,7-dimethyl4-bora-3a,4a-diaza-s-indacene-3-dodecanoyl)-1-hexadecanoyl-sn-glycero-3-phosphoethanolamine in 500 µL of chloroform is added 1.0 µL (0.006 mmol) of N,N-diisopropylethylamine followed by 2.5 mg (0.003 mmol) of Compound 5. The mixture is stirred for 16 hours, is then diluted with 15 mL of chloroform, washed with water, and evaporated. The resulting residue is purified by silica gel chromatography to give 2.0 mg of Compound 31 as a purple solid.

Example 21

Preoaration of a Rhodol Quenching Compound (32)

Compound 32

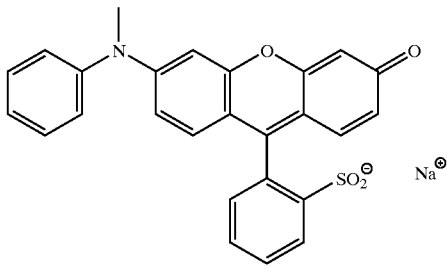

To 0.405 g of 3,6-dichlorosulfofluoran in 20 mL of acetonitrile at 0° C. is added 0.107 g of N-methylaniline. The mixture is warmed to room temperature and stirred overnight. The volatile components are removed under reduced pressure and 20 mL of dioxane is added, followed by 2 mL of an aqueous 10% solution of NaOH. The reaction mixture is heated at 60° C. for 4 hours to generate crude Compound 32, which is isolated by acidification with HCl, followed by chromatographic purification.

Example 22

Evaluation of Quenching Compound Fluorescence

Quantum yield measurements are made by comparing the integrated fluorescence emission of the quenching compound of the invention with the integrated fluorescence of nile blue (QY=0.23 in ethanol) at equal dye absorbance, at the excitation wavelength. The fluorescence of buffer alone is subtracted from that of the sample for each measurement. The quenching compounds of the invention are essentially non-fluorescent (Table 4).

TABLE 4

Spectral properties of selected compounds of the invention.

| Quencher | Absorbance maximum (nm) | Emission maximum (nm) | Quantum yield |
|---|---|---|---|
| DABCYL | 376 | nd | 0.0005[1] |
| | | | 0.0008[2] |
| Compound 2 | 560 | 604 | 0.0009 |
| Compound 5 | 561 | 608 | 0.0009 |
| Compound 8 | 660 | 760 | 0.0002 |
| Compound 10 | 558 | 609 | 0.001 |
| Compound 13 | 560 | 610 | 0.002 |
| Compound 16 | 649 | 714 | 0.0001 |
| Compound 27 | 553 | 599 | 0.002 |
| Compound 28 | 560 | 635 | 0.0002 |

TABLE 4-continued

Spectral properties of selected compounds of the invention.

| Quencher | Absorbance maximum (nm) | Emission maximum (nm) | Quantum yield |
|---|---|---|---|
| Compound F | 505 | 543 | nd |
| Compound H | 548 | 598 | 0.009 |
| Compound I | 574 | 570 | 0.006 |
| Compound J | 528 | 570 | nd |

[1]relative to fluorescein in TE buffer, pH 9.0, quantum yield 0.92.
[2]relative to quinine sulfate in 0.1 M perchloric acid, quantum yield 0.60.
nd = not determined Example 23

Quenching of a Fluorescent Dye-labeled Protein

Albumin from bovine serum (BSA), previously labeled with 6.3 moles of fluorescein per mole of protein, is dissolved in 0.1 M bicarbonate buffer (pH 8.3) to give a solution concentration of 5 mg/mL. Three aliquots of 0.4 mL (2 mg) are removed from the resulting solution, and are treated with DMSO solutions of Compound 5 equivalent to 5, 10, and 20 molar equivalents of Compound 5 per mole of BSA, respectively. Each of the resulting solutions are incubated for one hour at room temperature. Hydroxylamine is added (to a final concentration of 0.15 M) to stop the conjugation reaction. After the samples are incubated for 30 minutes at room temperature, they are subjected to size exclusion chromatography in 0.1 M sodium phosphate buffer (pH 8.0).

The fluorescence emission spectra of the fluorescent starting material and each of the resulting quenched conjugates is recorded by matching the conjugate absorbance at the excitation wavelength (480 nm). The degree of quenching of the conjugates is given in Table 5.

TABLE 5

| quenching compound:BSA ratio | Percent decrease in fluorescein fluorescence |
|---|---|
| 5:1 | 67.8% |
| 10:1 | 82.1% |
| 20:1 | 93.4% |

Example 24

Fluorescence Quenching of Fluorescent Avidin and Streptavidin Via Binding of Quenching Compound-labeled Biotin A variety of fluorescent dye-labeled avidin or streptavidin conjugates (Molecular Probes, Inc.) are treated with Compound 29, and the effect of binding the quenching compound labeled biotin on fluorescence is measured.

General procedure: Samples of each fluorescently labeled avidin or streptavidin conjugate (0.5 mg each) are dissolved in 0.1 M sodium phosphate (pH 7.5). To establish normal fluorescence, 0.5 mg of each conjugate is treated with non-labeled biotin dissolved in DMSO to obtain a final molar ratio of 10 moles of biotin per mole of protein. To evaluate fluorescence quenching, 0.5 mg of each conjugate is treated with Compound 29 at a final molar ratio of 10 moles of biotin conjugate per mole of protein. Each sample is incubated for one hour at room temperature, then purified using size exclusion chromatography in 0.1 M sodium phosphate (pH 7.5, or pH 8.0 in the case of avidin-fluorescein).

The fluorescence emission spectra of the quenched and control samples, matched for absorbance at the excitation wavelength, show that binding Compound 29 produces a decrease in the fluorescence, relative to the biotin control, in all cases.

TABLE 6

Percent Quenching upon Binding Compound 29:

| Protein-Dye Conjugate associated with Compound 29 | Dyes per Protein | $\lambda_{Ex}$ (nm) | Relative QY* | Percent Quenching |
|---|---|---|---|---|
| Avidin-fluorescein | 3.4 | 480 | 0.014 | 98.6 |
| Streptavidin-MARINA BLUE ™ | 5.2 | 350 | 0.072 | 92.8 |
| Streptavidin-ALEXA ™ 350 | 4.3 | 350 | 0.026 | 97.4 |
| Streptavidin-TEXAS RED ®-X | 3.1 | 560 | 0.003 | 99.7 |
| Streptavidin-RPE† | n. a. | 495 | 0.151 | 84.9 |
| Streptavidin-APC‡ | n. a. | 615 | 0.576 | 42.4 |

*Relative quantum yield is the quantum yield of the quenched protein-dye conjugate relative to the quantum yield of the free, unconjugated, fluorophore.
†RPE = R-phycoerythrin
‡APC = allophycocyanin Example 25

Preparation of Oliaonucleotide Conjugates of Quenching Compounds

Eighteen-base oligonucleotide conjugates of quencher dyes are prepared using standard methods. Typically, a C-6 TFA primary amine is synthetically incorporated on the 5' end of the oligonucleotide of interest as a phosphoramidite, and is subsequently reacted with a succinimidyl ester derivative of a quenching compound of the invention.

The succinimidyl ester derivative is dissolved in DMSO at a concentration of about 12.5 mg/mL. The amine-modified oligonucleotide is dissolved in water at a concentration of 25 mg/mL. A fresh solution of 0.1 M sodium borate, pH 8.5 is prepared. In a microfuge tube, 4 µL of the oligonucleotide solution is combined with 200 µg of the quenching compound solution and 100 µL sodium borate buffer. Samples are incubated 4 hours to overnight at room temperature, and the nucleic acids are precipitated by addition of 1/10$^{th}$ volume 0.3 M NaCl and 2.5 volumes cold absolute ethanol. Samples are incubated for 30 minutes at −20° C. and centrifuged at 15,000×g in a microfuge for 30 minutes. The supernatant fluid is decanted and the pellet dried under vacuum.

Alternatively, the oligonucleotide conjugate is prepared by reaction of a maleimide derivative of a quenching compound of the invention with an oligonucleotide that has been derivatized by a thiol that has been incorporated via a phosphoramidite.

Conjugates are further purified by reverse phase HPLC, using a C8 reverse phase column and a gradient of 5–95% acetonitrile in 0.1 M TEAA, pH 7. Absorbance and fluorescence emission spectra are determined in 10 mM Tris-HCl, 1 mM EDTA, pH 7.5. Quantum yield measurements are made as described above (Example 22). Oligonucleotide conjugates of the quenchers are essentially nonfluorescent (Table 7).

TABLE 7

Spectral properties of amine-oligonucleotide conjugates of the quencher dyes.

| Compound | Excitation wavelength (nm) | QY of the conjugate | Fluorescence increase relative to free dye |
|---|---|---|---|
| Compound 5 | 560 | 0.003 | 3.5-fold |
| Compound 8 | 630 | 0.0006 | 3-fold |
| Compound 13 | 560 | 0.004 | 2-fold |
| Compound 16 | 630 | 0.0008 | 4–8-fold |

The absorbance and emission maxima for the conjugates are shifted typically 5–15 nm relative to those of the free dye.

Example 26

Preparation of an Oliaonucleotide Conjugate, Substituted with both a Fluorophore and a Quenching Compound Oligonucleotides conjugated to a fluorescein fluorophore at one terminus and a quenching compound of the invention at the other terminus are prepared using a 3' or 5' fluorescein phosphoramidite and an amine modifier at the other terminus of the oligonucleotide, followed by labeling with a succinimidyl ester derivative of the invention (as described above in Example 25), or by synthesis of oligonucleotides containing an amino modifier on one terminus and a thiol at the other terminus, followed by sequential reaction with a maleimide derivative and succinimidyl ester derivative of the fluorophore and quenching compound, or vice versa. The fluorescence of the resulting conjugates is measured at equal conjugate concentration. Selected compounds of the instant invention quench the fluorescence of fluorescein much more efficiently than does DABCYL and all of the quenchers quench tetramethylrhodamine much more efficiently than does DABCYL (as shown in Table 8).

TABLE 8

The fluorescence of selected fluorophore-labeled and quenching compound-labeled eighteen-base oligonucleotides.

| Quenching compound | Fluorescence emission relative to unquenched fluorescein conjugate | Fluorescence emission relative to unquenched tetramethylrhodamine conjugate |
|---|---|---|
| None | 100% | 100% |
| DABCYL | 14% | 92% |
| Compound 5 | 4.5% | 6% |
| Compound 8 | 12% | 3% |
| Compound 13 | 12% | — |
| Compound 16 | 4.5% | 4% |

Example 27

Preparation of Doubly Labeled Olizonucleotide Conjugates

Random-sequence oligonucleotides 10, 20, 30 and 40 bases in length are labeled with fluorescein at their 3' terminus using a fluorescein phosphoramidite, and with Compound 5 or DABCYL at their 5' terminus, by reacting the amine-modified oligonucleotide with the succinimidyl ester derivative (as described above, Example 2). Resulting conjugates are purified by reverse phase HPLC. The fluorescence of equal amounts of these doubly labeled conjugates is determined relative to the fluorescence of fluorescein conjugates lacking the quencher dye. Compound 5 quenches the fluorescein conjugates more efficiently than DABCYL does, until the conjugates reach about 30 bases in length.

TABLE 9

Relative % fluorescence intensity of the quencher conjugates compared to unquenched fluorescein conjugates of the same length.

| Oligonucleotide length (in bases) | DABCYL | Compound 5 |
|---|---|---|
| 10 | 17 | 2.3 |
| 20 | 49 | 18 |
| 30 | 62 | 46 |
| 40 | 58 | 62 |

Example 28

Hybridization of Doubly-labeled Oligonucleotide Conjugates to Unlabeled Complementary Olizonucleotides Solutions are prepared containing 1 μg/mL 18-base oligonucleotide conjugates of a quenching compound of the invention attached to the 5' terminus, as well as a fluorescein or tetramethylrhodamine fluorophore on the 3' terminus. The oligonucleotide conjugates are hybridized with 40 μg/mL reverse complement oligonucleotide in TE buffer at pH 9.0. The samples are heated for 10 minutes at 65° C., allowed to cool slowly to room temperature, and are then incubated at room temperature for 60 minutes, protected from light. A portion of each sample is transferred to a microplate well and the fluorescence emission of the sample is determined at 530±9 nm (with 480±9 nm excitation) for fluorescein and at 580±9 nm (with 535±9 nm excitation) for tetramethylrhodamine. In each case, the fluorescence is compared to the fluorescence of a buffer solution alone.

All of the conjugates of the invention exhibit an increase in fluorescence upon hybridization, even oligonucleotides labeled with fluorescein or tetramethylrhodamine alone (Table 10).

TABLE 10

Effect of hybridization on fluorescence quenching.

| | % Fluorescence Recovered upon Hybridization* | |
|---|---|---|
| Quenching Compound | Fluorescein | Tetramethylrhodamine |
| None | 113% | 230% |
| DABCYL | 33% | 140% |
| Compound 5 | 31% | 111% |
| Compound 8 | 35% | 49% |
| Compound 13 | 35% | nd |
| Compound 16 | 34% | 27% |

*The fluorescence exhibited by the double-labeled oligonucleotide upon hybridization, divided by the fluorescence exhibited by an oligonucleotide labeled with the fluorophore alone.

Because the quenched oligonucleotides initially exhibited extremely low fluorescence, they show larger increases upon hybridization, and therefore the conjugates that are the most efficiently quenched prior to hybridization exhibit the largest increase in fluorescence. This property is utilized to formulate a homogenous assay method to detect the presence of to specific complementary DNA sequences in a sample. Several of the compounds of the invention quench fluorescence more efficiently than DABCYL in this application. Similarly, doubly labeled oligonucleotides that form structures that enhance quenching, such as hairpin or stem loop structures, as in BEACON probes, can also be used in this application.

TABLE 11

Fluorescence enhancement upon hybridization.

| Quenching Compound | Fluorescence Enhancement* | |
|---|---|---|
| | Fluorescein label | Tetramethylrhodamine label |
| None | 1.1 | 2.3 |
| DABCYL | 2.4 | 1.4 |
| Compound 5 | 6.3 | 19 |
| Compound 8 | 2.9 | 7 |
| Compound 13 | 2.8 | nd |
| Compound 16 | 8.2 | 19 |

*The observed increase in fluorescence of the double-labeled oligonucleotide upon hybridization.

Example 29

Hybridizing Oliaonucleotide Conjugates of Quenching Compounds with Fluoroohore Labeled Oligonucleotides Oligonucleotides conjugated to a quenching compound at one terminus quench the fluorescence of fluorophore labeled nucleotides upon hybridization. Labeled oligonucleotides are prepared as described above (Examples 25 and 26), and hybridized with their reverse complements. Samples containing 2 μg/mL quenching compound-labeled 18 base oligonucleotides and 200 ng/mL fluorescein-labeled reverse complement oligonucleotides in 10 mM Tris-HCl, 1 mM EDTA, pH 9.0, are hybridized and their fluorescence is determined as described above (Example 22). The quenching compound oligonucleotides efficiently quench the fluorescence of fluorescein that is localized at the same end of hybridized oligonucleotides, but quench the fluorescence of distant fluorophores more poorly.

TABLE 12

Effect of fluorophore quenching compound proximity on quenching efficiency.

| | Relative Fluorescence of the hybrid (%)[1] | |
|---|---|---|
| Quencher | 3'-end label[2] | 5'-end label[2] |
| None | 79 | 75 |
| DABCYL | 14 | 98 |
| Compound 5 | 6.6 | 68 |
| Compound 8 | 11 | 89 |
| Compound 13 | 10 | 82 |
| Compound 16 | 13 | 84 |

[1]Relative fluorescence is the fluorescence of the hybrid divided by that obtained for the fluorophore-labeled oligonucleotide alone.
[2]The position of the end label indicates the position of the fluorophore label on the reverse complement oligonucieotide. The quenching compound is attached at the 5' terminus of the oligonucleotide.

Example 30

Quenching Fluorescence of Nucleotides Added Enzymatically to the 3' End of a Primer An eighteen-base oligonucleotide is labeled with Compound 5 on its 5' terminus, as described above (Example 25). The resulting conjugate is incubated with terminal deoxynucleotidyl transferase under standard assay conditions for 3' end elongation, in the presence of fluorophore-labeled dUTP conjugates, as follows: The oligonucleotide conjugate (650 ng) is incubated with 1 μL of 25 mM fluorophore-labeled nucleotide, 0.5 mM $CoCl_2$, and 0.2 M potassium cacodylate, 25 mM Tris-HCl, pH 6.6, 2 mM DTT, and 250 μg/mL bovine serum albumin for 60 minutes at 37° C. A one-fifth volume of a solution containing 50% glycerol and 0.01% bromophenol blue is added to each reaction, and the samples are separated by electrophoresis on a 20% polyacrylamide/8 M urea minigel in TBE buffer (45 mM Tris-borate, 1 mM EDTA), under conditions that resolve single nucleotide additions to the oligonucleotide. Samples containing oligonucleotides that are lacking the quenching compound are processed in parallel, for use as size standards. Gels are visualized using a 300-nm UV transilluminator combined with Polaroid black and white photography, or using a laser scanner. The gels are post-stained with a fluorescent nucleic acid stain, such as SYBR® Gold stain, and band fluorescence is visualized in the same way. The size of the oligonucleotides is determined based on comparisons of electrophoretic migration with the unlabeled standard. Quenching is detected as lack of fluorescence or visibility of a band of a particular size from the pattern visible in the standard. Where the fluorophore is fluorescein or Texas Red® dye, the label fluorescence is readily quenched by the 5'-bound quenching compound. The fluorescence of Cascade Blue® dye is not as efficiently quenched. As additional nucleotides are added, the ones most distant from the quenching compound begin to exhibit fluorescence.

This technique is useful as a gel-based method for quantitating terminal transferase activity. Enzyme activity in an unknown sample is determined by comparison of the number of added nucleotides per template or the number of templates with added nucleotides of a certain length with the numbers obtained using a standard amount of enzyme activity following a standard reaction time interval.

Example 31

Quenching of a Fluorescent Olivonucleotide by Enzymatic Incorporation of a Quenching Compound Conjugate of Nucleotide Trinhosphate Via Primer Extension A short oligonucleotide, having 6 to about 20 bases, is labeled with a fluorophore such as fluorescein, tetramethylrhodamine or Texas Red® dye, on its 5' terminus, and then purified via HPLC using standard methods (as described above, Examples 25 and 26). For template-driven reactions, the oligonucleotide is hybridized to an appropriate template, and incubated with a quenching compound-labeled nucleotide or deoxynucleotide in an appropriate buffered solution, in the presence of samples thought to contain an appropriate DNA or RNA polymerase. Enzyme activity is determined by measuring the rate of fluorescence loss from the solution, versus the rate of loss observed from solutions containing known amounts of enzyme activity. Terminal deoxynucleotidyltransferase activity is assayed by determining the rate of fluorescence loss from the solution upon incubation with samples thought to contain terminal deoxynucleotidyltransferase activity. For measurement of terminal deoxynucleotidyl transferase activity, fluorophore-labeled templates are incubated with quenching compound-labeled nucleotides in the buffer described above (Example 33) for a set time interval, and fluorescence is measured in a fluorescence microplate reader or fluorometer.

To measure reverse transcriptase activity, 2 μg mRNA is combined with 5 μg fluorophore labeled poly dT(16) oligomer in 10 mM Tris-HCl, pH. 8.0, 1 mM EDTA; the mixture is heated to 70° C. for 10 minutes and then chilled on ice. A solution containing 2 μL reverse transcriptase (200 units/μL for the standard, or unknown amounts), 500 μM dATP, 500 μM dCTP, 500 μM dGTP, 200 μM dTTP, and 60 μM quenching compound-labeled dUTP is prepared and added to the RNA. The reaction is allowed to proceed for 2 hours at 42° C. The fluorescence of the solution is measured in a fluorescence microplate reader or fluorometer versus a standard. The decrease in fluorescence in comparison to samples lacking enzyme activity is directly related to the activity of the enzyme in the reaction.

To measure KIenow DNA polymerase activity, 1 μg random sequence 9-mer oligonucleotides labeled with a fluorescent dye are combined with 2.5 μg genomic DNA in 10 mM Tris-HCl, pH 8.0, 1 mM EDTA. The mixture is boiled for 2 minutes and chilled on ice. A reaction mixture containing 25 μM dATP, 25 μM dCTP, 25 μM dGTP and 10 μM dTTP, plus 40 μM quenching compound-labeled dUTP in 1 mM Tris-HCl, pH 7.5, 5 mM NaCl, 0.01 mM EDTA, pH 8.0, 5 mM dithiothreitol is combined with samples thought to contain DNA polymerase. The reaction mixture is combined with the DNA mixture and incubated at 37° C. for 2 hours. The fluorescence of the sample is measured versus standards, as described above.

Example 32

Using Quenching Compounds to Measure Nuclease Activity

Oligonucleotide conjugates labeled with both a quenching compound at one terminus and a fluorophore at the other terminus are prepared as described above (Examples 25 and 26). For measuring single-stranded nuclease activity, the conjugates are incubated in the presence of samples thought to contain nuclease activity in the presence of an appropriate buffer and the resulting fluorescence increase in the sample is compared to that obtained using standards of known nuclease concentration. To measure double-stranded nuclease activity, double-stranded templates are prepared by hybridizing two oligonucleotides to one another, or by chemically modifying a double-stranded template using reagents such as platinum complexes of fluorophores and quenchers (as described above), or by using an enzyme such as a terminal transferase to add nucleotides to the end of a template (as described above in Examples 30 and 31). Samples thought to contain nuclease activity are incubated with such templates in the presence of appropriate buffers and the increase in fluorescence compared to a standard, as described above.

Example 33

Using Quenching Compounds to Measure Ligase Activity

Oligonucleotide hexamers labeled at the 5' terminus with a quenching compound are prepared as described above. Oligonucleotide hexamers labeled with a fluorophore at the 3' terminus and phosphate at the 5' terminus are prepared as described above excepting that the phosphate is alternatively applied by standard methods using a phosphoramidite or by enzymatic means, such as T4 polynucleotide kinase.

A reaction mixture is prepared that contains about 5 μg of each oligonucleotide conjugate, 0 0.5 mM ATP, and samples thought to contain ligase activity, in 1 mM $MgCl_2$, 2 mM dithiothreitol, 5 μg/mL bovine serum albumin, and 5 mM Tris-HCl, pH 7.7, in a volume of 20 µL. The reaction mixtures are incubated for 2 hours to overnight at 22° C., and the sample fluorescence is measured. As the quenching compound-labeled oligonucleotides do not contain a free 5' phosphate, they cannot ligate to one another, and as the fluorophore-labeled oligonucleotides do not contain a free 3' hydroxyl, they cannot ligate to one another. Thus the only products of ligation will be a dimer of the two oligonucleotides and the fluorescence decrease observed during the course of the reaction is a measure of ligase activity. Alternatively, RNA oligonucleotides are used as templates to measure RNA ligase activity or splicing activity.

Example 34

Labeling Large DNA Molecules with Platinum Cuenching Compound Complexes

A quenching compound platinum complex is synthesized by adapting the methods provided in U.S. Pat. No. 5,714,327 to Houthoff et. al. (1998) and a 1 mg/mL solution of the quenching compound complex is prepared in water. This solution is then diluted into water, and 10 ng to 3 µg of the quenching compound complex is added to a microfuge tube containing 500 ng of plasmid DNA. The volume is brought up to 25 µL with water, and the samples heated at 65° C. for 15 minutes. Five µL of 1% diethyldithiocarbamic acid sodium salt solution is added to stop the reaction, samples are mixed and cooled to room temperature, and 10 µL of each reaction is loaded onto a 1% agarose minigel. The gel is electrophoresed in 0.5×TBE buffer (45 mM Tris-borate, 1 mM EDTA, pH 8), stained with SYBR® Gold stain, and photographed with 300 nm transillumination, through a SYBR® Gold photographic filter. Samples labeled with 10 ng to 0.3 µg of the quenching compound complex are very fluorescent. Samples labeled with 0.5 µg to 1 µg of the quenching compound complex show only weak fluorescence. Samples labeled with 1.5 µg to 3 µg of the quenching compound complex are essentially non-fluorescent. Similarly, samples labeled with sufficient amounts of the quenching compound complex are able to quench the fluorescence of bound hybridization probes that are themselves labeled with reactive fluorophore labels or fluorescent nucleotides.

Example 35

Preparation of Quenched Double-stranded DNA

Oligonucleotides are prepared that are either labeled with a fluorophore at a strand terminus, or within the oligonucleotide sequence itself, using standard methods as described above. The oligonucleotides are then used as primers for PCR or are otherwise enzymatically extended using standard methods. A quenching compound platinum complex is prepared (as described in U.S. Pat. No. 5,714,327 to Houthoff et. al. (1998)) and dissolved in water at a final concentration of 1 mg/mL. DNA (500 ng) is combined with 1.5 µg of the quenching compound platinum complex and incubated in a total volume of 25 µL water for 15 minutes at 65° C. The reaction is chilled in an ice bath to stop it. The quenched DNA is not visible after gel electrophoresis, even when stained with a fluorescent nucleic acid stain or incubation in solution with a fluorescent nucleic acid stain.

Example 36

Using Quenching Compounds to Assay Topoisomerase Activity

Quenched DNA is prepared as described above, using a circular single stranded DNA template, such as an M13 or φX174 phage DNA genome, and a quenching compound platinum complex (Example 34). A fluorophore-labeled oligonucleotide is then hybridized to the quenched DNA. Samples thought to contain topoisomerase activity are combined with the template under optimal reaction conditions for the enzyme, and the reaction is allowed to proceed for an appropriate period of time. Enzyme activity is measured as fluorescence increase for the solution, using a fluorescence microplate reader or fluorometer.

Example 37

Detection of Phospholipase Activity

A 10 µM solution of the phospholipase substrate Compound 31 in 100 mM Tris-HCl, pH 8.0, 0.5 mM $CaCl_2$ is prepared. Aliquots of the solution are then incubated at 37° C. with varying concentrations of the calcium-dependent phospholipase enzyme $PLA_2$ for up to 120 minutes. Upon incubation, the solution becomes highly fluorescent. In the absence of $PLA_2$, however, the sample solution remains essentially nonfluorescent.

The enzymatic activity of $PLA_2$ is detected by measuring the fluorescence intensities of the reaction mixtures using a fluorescence plate reader with the standard filter set for fluorescein. Fluorescence intensity correlates very well with the enzyme activity of $PLA_2$ (correlation coefficient of 0.9995, see FIG. 1). However, there is no change of fluorescence when the substrate is incubated with $PLA_2$ in the buffer without 0.5 mM $CaCl_2$, or in the presence of 2 mM EGTA, indicating that this $PLA_2$ (Sigma P-6534) is highly calcium-dependent.

It is to be understood that, while the foregoing invention has been described in detail by way of illustration and example, numerous modifications, substitutions, and alterations are possible without departing from the spirit and scope of the invention as described in the following claims.

What is claimed is:

1. A compound, having the formula

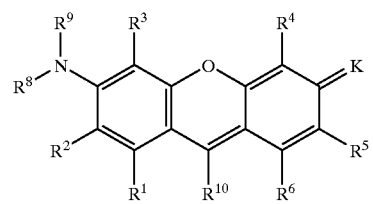

wherein
$R^1$ is H; $R^6$ is H;
$R^2$, $R^3$, $R^4$ and $R^5$ are independently H, F, Cl, Br, I, CN; or $C_1$–$C_{18}$ alkyl, or $C_1$–$C_{18}$ alkoxy,
where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$
where X is H or a counterion;
or $R^1$ taken in combination with $R^2$, or $R^6$ taken in combination with $R^5$ is a fused six-membered aromatic ring;
$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or —L—$R_x$; or —L—$S_c$; or one or more of $R^8$ and $R^9$ is a Q moiety; or $R^8$ taken in combination with $R^9$ forms a saturated 5- or 6-membered heterocycle that is optionally fused to a Q moiety and said heterocycle is optionally further substituted by methyl, carboxylic acid, a salt of carboxylic acid, a carboxylic acid ester of a $C_1$–$C_6$ alkyl, or by —L—$R_x$, or —L—$S_c$;

wherein each Q moiety is 1–4 aromatic or heteroaromatic rings that is optionally substituted by halogen, cyano, sulfo, alkali or ammonium salt of sulfo, carboxy, alkali or ammonium salt of carboxy, nitro, alkyl, perfluoroalkyl, alkoxy, alkylthio, amino, monoalkylamino, dialkylamino; alkylamido; or is substituted by —L—$R_x$; or is substituted by —L—$S_c$; wherein each heteroaromatic ring in Q is a 5- or 6-membered aromatic heterocycle having 1 to 3 heteroatoms selected from the group consisting of O, N or S in any combination; and when Q is 2–4 rings, said 2–4 rings are fused to each other; and K is O or $N^+R^{18}R^{19}$;

wherein $R^{18}$ and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or —L—$R_x$; or —L—$S_c$; or one or more of $R^{18}$ and $R^{19}$ is a Q moiety; or $R^{18}$ taken in combination with $R^{19}$ forms a saturated heterocyclic ring that is a morpholine, a pyrazine, or a piperazine, that is optionally substituted by methyl, sulfonic acid, a salt of sulfonic acid, carboxylic acid, a salt of carboxylic acid, or a carboxylic acid ester of a $C_1$–$C_6$ alkyl; or $R^{18}$ taken in combination with $R^{19}$ forms a saturated 5- or 6-membered heterocycle that is a piperidine, or a pyrrolidine that is optionally fused to a Q moiety, and the heterocycle is optionally further substituted by methyl, carboxylic acid, a salt of carboxylic acid, a carboxylic acid ester of a $C_1$–$C_6$ alkyl, or by —L—$R_x$, or —L—$S_c$;

$R^{10}$ is H, CN, a carboxylic acid, a salt of carboxylic acid, or a carboxylic acid ester of a $C_1$–$C_6$ alcohol; or $R^{10}$ is a saturated or unsaturated $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino, the alkyl groups of which have 1–6 carbons; or $R^{10}$ has the formula

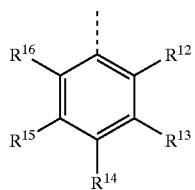

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid; or one of $R^{12}$, $R^{13}$, $R^{14}$, $R^{15}$ and $R^{16}$ is —L—$R_x$ or —L—$S_c$;

provided that at least one of $R^8$, $R^9$, $R^{18}$, and $R^{19}$ is, or is fused to, a Q moiety; and further provided that at least one of $R^8$, $R^9$, $R^{12}$, $R^{13}$, $R^{14}$, $R^{15}$, $R^{16}$, $R^{18}$, or $R^{19}$ is —L—$R_x$ or —L—$S_c$; or at least one Q moiety is substituted by —L—$R_x$ or —L—$S_c$; wherein L is a covalent linkage; and $R_x$ is a reactive functional group that is a maleimide, isocyanate, isothiocyanate, a phosphoramidite, a reactive platinum complex, perfluorobenzamido, azidoperfluorobenzamido, a succinimidyl ester, a sulfosuccinimidyl ester, an alkali or alkaline earth metal salt of a sulfosuccinimidyl ester, a symmetric anhydride, a mixed anhydride of a chloroformate having 2–8 carbons, a mixed anhydride of a carboxylic acid or perfluorinated carboxylic acid having 2–8 carbons, a mixed anhydride of a sulfonic acid or fluorinated sulfonic acid having 1–8 carbons, or an ester of a phenol or a naphthol that is further substituted one or more times by nitro, sulfo, carboxy, alkali or alkaline earth metal salt of sulfo or carboxy, cyano, fluoro, chloro, or trifluoromethyl; or $R_x$ is the adduct of a carboxylic acid and a carbodiimide having 2–14 carbons; and $S_c$ is a conjugated substance.

2. A compound, as claimed in claim 1, wherein the conjugated substance is an antigen, a steroid, a vitamin, a drug, a hapten, a metabolite, a toxin, an environmental pollutant, an amino acid, a peptide, a protein, a nucleotide, an oligonucleotide, a nucleic acid polymer, a carbohydrate, a lipid, an ion-complexing moiety, or a non-biological polymer.

3. A compound as claimed in claim 1, wherein the conjugated substance is an amino acid, a peptide, a protein, a nucleotide, an oligonucleotide, a nucleic acid polymer, a carbohydrate, a lipid, or a drug.

4. A compound as claimed in claim 1, wherein the conjugated substance is a hapten or a member of a specific binding pair.

5. A compound as claimed in claim 1, wherein the conjugated substance is further conjugated to one or more luminophores, where each luminophore may be the same or different.

6. A compound, as claimed in claim 5, wherein at least one of the luminophores is a fluorophore.

7. A compound, as claimed in claim 6, wherein the fluorophore is a pyrene, an anthracene, a naphthalene, an acridine, a stilbene, an indole, a benzindole, an oxazole, a benzoxazole, a thiazole, a benzothiazole, a 4-amino-7-nitrobenz-2-oxa-1,3-diazole, a cyanine, a carbocyanine, a carbostyryl, a porphyrin, a salicylate, an anthranilate, an azulene, a perylene, a pyridine, a quinoline, a coumarin, a polyazaindacene, a xanthene, an oxazine, a benzoxazine, a carbazine, a phenalenone, or a benzphenalenone.

8. A compound, as claimed in claim 6, wherein the fluorophore is a carbazine, an oxazine, a coumarin, a pyrene, a xanthene, a naphthalene, a phenalenone, or a 4-bora-3a, 4a-diaza-s-indacene.

9. A compound, as claimed in claim 6, wherein the fluorophore is a fluorescein, a rhodamine, or a rhodol.

10. A compound as claimed in claim 1, wherein each Q moiety is a substituted or unsubstituted phenyl, naphthyl, anthracenyl, benzothiazole, benzoxazole, or benzimidazole.

11. A compound, as claimed in claim 1, wherein each Q moiety is a phenyl or substituted phenyl.

12. A compound, as claimed in claim 1 wherein K is $N+R^{18}R^{19}$.

13. A compound, as claimed in claim 1, wherein $R^8$ taken in combination with $R^9$ forms a saturated 5- or 6-membered heterocycle that is fused to a Q moiety, and $R^{18}$ taken in combination with $R^{19}$ forms a saturated 5- or 6-membered heterocycle that is fused to a Q moiety.

14. A compound, as claimed in claim 1, wherein $R^8=R^{19}$ and $R^9=R^{18}$.

15. A compound, as claimed in claim 1, wherein $R^1$, $R^2$, $R^5$, and $R^6$ are each H.

16. A compound, as claimed in claim 1, wherein $R^{10}$ has the formula

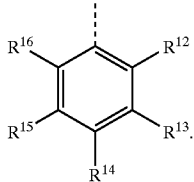

17. A compound, as claimed in claim 16, wherein one of $R^{12}$–$R^{16}$ is —L—$R_x$ or —L—$S_c$.

18. A compound, as claimed in claim 16, wherein $R^{12}$ is —L—$R_x$;

wherein L is selected such that —L—$R_x$ has the formula

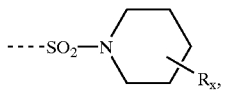

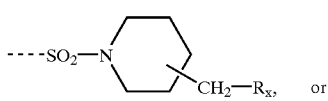

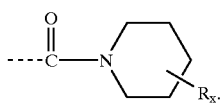

19. A compound, as claimed in claim 1, wherein $R_x$ is a phosphoramidite, a reactive platinum complex, a succinimidyl ester of a carboxylic acid, a haloacetamide, a hydrazine, an isothiocyanate, a maleimide group or an azidoperfluorobenzamido group.

20. A compound, as claimed in claim 1, wherein $R_x$ is a phosphoramidite, a reactive platinum complex, or a succinimidyl ester of a carboxylic acid.

21. A compound, as claimed in claim 1, having the formula

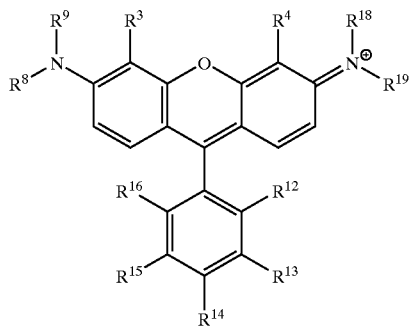

wherein
$R^8=R^{19}$ and $R^9=R^{18}$;
$R^{12}$ is —L—$R_x$, or —L—$S_c$; and
each Q moiety is a substituted or unsubstituted phenyl, naphthyl, anthracenyl, berzothiazole, benzoxazole, or benzimidazole.

22. A compound, as claimed in claim 1, having a fluorescence quantum yield of less than about 0.05.

23. A method of detecting a change in separation distance between one or more luminophore donors and quenching compound acceptors in a sample, wherein at least one quenching compound acceptor has the formula

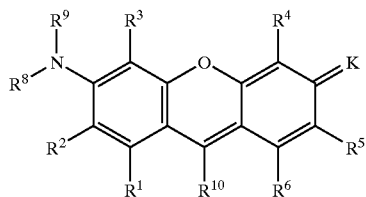

wherein
$R^1$ is H; $R^6$ is H;
$R^2$, $R^3$, $R^4$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$ where X is H or a counterion;

or $R^1$ taken in combination with $R^2$, or $R^6$ taken in combination with $R^5$ is a fused six-membered aromatic ring;

$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or —L—$R_x$; or —L—$S_c$; or one or more of $R^8$ and $R^9$ is a Q moiety; or $R^8$ taken in combination with $R^9$ forms a saturated 5- or 6-membered heterocycle that is optionally fused to a Q moiety and said heterocycle is optionally further substituted by methyl, carboxylic acid, a salt of carboxylic acid, a carboxylic acid ester of a $C_1$–$C_6$ alkyl, or by —L—$R_x$, or —L—$S_c$;

wherein each Q moiety is 1–4 aromatic or heteroaromatic rings that is optionally substituted by halogen, cyano, sulfo, alkali or ammonium salt of sulfo, carboxy, alkali or ammonium salt of carboxy, nitro, alkyl, perfluoroalkyl, alkoxy, alkylthio, amino, monoalkylamino, dialkylamino; alkylamido; or is substituted by —L—$R_x$; or is substituted by —L—$S_c$; wherein each heteroaromatic ring in Q is a 5- or 6-membered aromatic heterocycle having 1 to 3 heteroatoms selected from the group consisting of O, N or S in any combination; and when Q is 2–4 rings, said 2–4 rings are fused to each other; and K is O or $N^+R^{18}R^{19}$;

wherein $R^{18}$ and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or —L—$R_x$; or —L—$S_c$; or one or more of $R^{18}$ and $R^{19}$ is a Q moiety; or $R^{18}$ taken in combination with $R^{19}$ forms a saturated heterocyclic ring that is a morpholine, a pyrazine, or a piperazine, that is optionally substituted by methyl, sulfonic acid, a salt of sulfonic acid, carboxylic acid, a salt of carboxylic acid, or a carboxylic acid ester of a $C_1$–$C_6$ alkyl; or $R^{18}$ taken in combination with $R^{19}$ forms a saturated 5- or 6-membered heterocycle that is a piperidine, or a pyrrolidine that is optionally fused to a Q moiety, and the heterocycle is optionally further substituted by methyl, carboxylic acid, a salt of carboxylic acid, a carboxylic acid ester of a $C_1$–$C_6$ alkyl, or by —L—$R_x$, or —L—$S_c$;

$R^{10}$ is H, CN, a carboxylic acid, a salt of carboxylic acid, or a carboxylic acid ester of a $C_1$–$C_6$ alcohol; or $R^{10}$ is a saturated or unsaturated $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino, the alkyl groups of which have 1–6 carbons; or $R^{10}$ has the formula

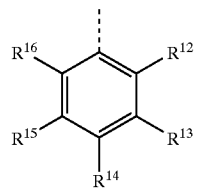

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid, or one of $R^{12}$, $R^{13}$, $R^{14}$, $R^{15}$ and $R^{16}$ is —L—$R_x$ or —L—$S_c$;

provided that at least one of $R^8$, $R^9$, $R_{18}$, and $R^{19}$ is, or is fused to, a Q moiety; and further provided that at least one of $R^8$, $R^9$, $R^{12}$, $R^{13}$, $R^{14}$, $R^{15}$, $R^{16}$, $R^{18}$, or $R^{19}$ is —L—$R_x$ or —L—$S_c$; or at least one Q moiety is substituted by —L—$R_x$ or —L—$S_c$; wherein L is a covalent linkage; and $R_x$ is a reactive functional group that is a maleimide, isocyanate, isothiocyanate, a phosphoramidite, a reactive platinum complex, perfluorobenzamido, azidoperfluorobenzamido, a succinimidyl ester, a sulfosuccinimidyl ester, an alkali or alkaline earth metal salt of a sulfosuccinimidyl ester, a symmetric anhydride, a mixed anhydride of a chloroformate having 2–8 carbons, a mixed anhydride of a carboxylic acid or perfluorinated carboxylic acid having 2–8 carbons, a mixed anhydride of a sulfonic acid or fluorinated sulfonic acid having 1–8 carbons, or an ester of a phenol or a naphthol that is further substituted one or more times by nitro, sulfo, carboxy, alkali or alkaline earth metal salt of sulfo or carboxy, cyano, fluoro, chloro, or trifluoromethyl; or $R_x$ is the adduct of a carboxylic acid and a carbodiimide having 2–14 carbons; and $S_c$ is a conjugated substance;

said method comprising the steps of:
a) illuminating said sample;
b) detecting a first luminescence response of said sample;
c) exposing said sample to an environmental condition expected to change said separation distance;
d) illuminating said sample;
e) detecting a second luminescence response of said sample; and
f) comparing said first and second luminescence response to determine a detectable difference in luminescence, where said detectable difference in luminescence correlates with said change in separation distance.

24. A method, as claimed in claim 23, wherein said detectable difference is an increase in luminescence.

25. A method, as claimed in claim 23, wherein said detectable difference is a decrease in luminescence.

26. A method, as claimed in claim 23, wherein said luminescence is fluorescence.

27. A method, as claimed in claim 23, wherein said quenching compound acceptor is initially covalently bound to a conjugated substance.

28. A method, as claimed in claim 27, wherein said luminophore donor is initially covalently conjugated to the same conjugated substance.

29. A method, as claimed in claim 28, wherein the conjugated substance is cleaved by said environmental condition, resulting in an increase in luminescence.

30. A method, as claimed in claim 28, wherein the conjugated substance changes conformation in response to said environmental condition, resulting in said detectable difference in luminescence.

31. A method, as claimed in claim 27, wherein the conjugated substance is an oligonucleotide, nucleic acid polymer, peptide or protein.

32. A method, as claimed in claim 27, wherein the conjugated substance is a member of a specific binding pair.

33. A kit for labeling a substance, comprising:
a) a quenching compound of the formula

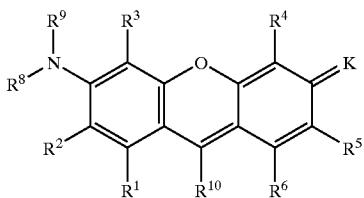

wherein
$R^1$ is H; $R^6$ is H;
$R^2$, $R^3$, $R^4$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$ where X is H or a counterion;
or $R^2$ taken in combination with $R^2$, or $R^6$ taken in combination with $R^5$ is a fused six-membered aromatic ring;
$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or —L—$R_x$; or one or more of $R^8$ and $R^9$ is a Q moiety; or $R^8$ taken in combination with $R^9$ forms a saturated 5- or 6-membered heterocycle that is optionally fused to a Q moiety and said heterocycle is optionally further substituted by methyl, carboxylic acid, a salt of carboxylic acid, a carboxylic acid ester of a $C_1$–$C_6$ alkyl, or by —L—$R_x$,
wherein each Q moiety is 1–4 aromatic or heteroaromatic rings that is optionally substituted by halogen, cyano, sulfo, alkali or ammonium salt of sulfo, carboxy, alkali or ammonium salt of carboxy, nitro, alkyl, perfluoroalkyl, alkoxy, alkylthio, amino, monoalkylamino, dialkylamino; alkylamido; or is substituted by —L—$R_x$; wherein each heteroaromatic ring in Q is a 5- or 6-membered aromatic heterocycle having 1 to 3 heteroatoms selected from the group consisting of O, N or S in any combination; and when Q is 2–4 rings, said 2–4 rings are fused to each other; and
K is O or $N^+R^{18}R^{19}$;
wherein $R^{18}$ and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or —L—$R_x$; or one or more of $R^{18}$ and $R^{19}$ is a Q moiety; or $R^{18}$ taken in combination with $R^{19}$ forms a saturated heterocyclic ring that is a morpholine, a pyrazine, or a piperazine, that is optionally substituted by methyl, sulfonic acid, a salt of sulfonic acid, carboxylic acid, a salt of carboxylic acid, or a carboxylic acid ester of a $C_1$–$C_6$ alkyl; or $R^{18}$ taken in combination with $R^{19}$ forms a saturated 5- or 6-membered heterocycle that is a piperidine, or a pyrrolidine that is optionally fused to a Q moiety, and the heterocycle is optionally further substituted by methyl, carboxylic acid, a salt of carboxylic acid, a carboxylic acid ester of a $C_1$–$C_6$ alkyl, or by —L—$R_x$;

$R^{10}$ is H, CN, a carboxylic acid, a salt of carboxylic acid, or a carboxylic acid ester of a $C_1$–$C_6$ alcohol; or $R^{10}$ is a saturated or unsaturated $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino, the alkyl groups of which have 1–6 carbons; or $R^{10}$ has the formula

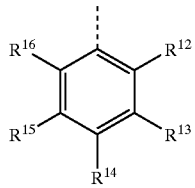

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid; or one of $R^{12}$, $R^{13}$, $R^{14}$, $R^{15}$ and $R^{16}$ is —L—$R_x$;
provided that at least one of $R^8$, $R^9$, $R^{18}$, and $R^{19}$ is, or is fused to, a Q moiety; and
further provided that at least one of $R^8$, $R^9$, $R^{12}$, $R^{13}$, $R^{14}$, $R^{15}$, $R^{16}$, $R^{18}$, or $R^{19}$ is —L—$R_x$; or at least one Q moiety is substituted by —L—$R_x$; wherein
L is a covalent linkage; and
$R_x$ is a reactive functional group that is a maleimide, isocyanate, isothiocyanate, a phosphoramidite, a reactive platinum complex, perfluorobenzamido, azidoperfluorobenzamido, a succinimidyl ester, a sulfosuccinimidyl ester, an alkali or alkaline earth metal salt of a sulfosuccinimidyl ester, a symmetric anhydride, a mixed anhydride of a chloroformate having 2–8 carbons, a mixed anhydride of a carboxylic acid or perfluorinated carboxylic acid having 2–8 carbons, a mixed anhydride of a sulfonic acid or fluorinated sulfonic acid having 1–8 carbons, or an ester of a phenol or a naphthol that is further substituted one or more times by nitro, sulfo, carboxy, alkali or alkaline earth metal salt of sulfo or carboxy, cyano, fluoro, chloro, or trifluoromethyl; or $R_x$ is the adduct of a carboxylic acid and a carbodiimide having 2–14 carbons; and
b) instructions for conjugating said quenching compound to said substance; and
c) one or more of the following: a buffering agent, a purification medium, a sample of said substance, an organic solvent, an enzyme, or an enzyme inhibitor.

34. A kit, as claimed in claim 33, wherein $R_x$ is a phosphoramidite, a reactive platinum complex, or a succinimidyl ester of a carboxylic acid.

35. A kit, as claimed in claim 33, wherein said substance is an oligonucleotide, nucleic acid polymer, peptide or protein.

36. A kit, as claimed in claim 33, wherein said substance is a member of a specific binding pair.

37. A kit, as claimed in claim 33, wherein said quenching compound has the formula

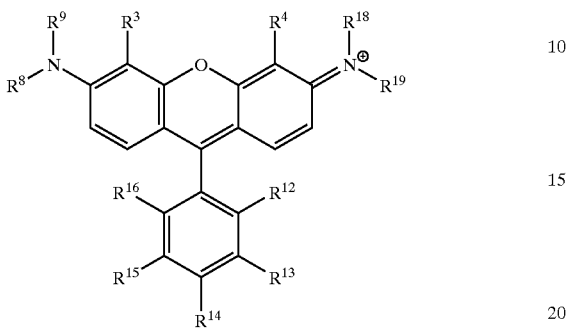

wherein
$R^{12}$ is —L—$R_x$; and
$R_x$ is a phosphoramidite, a reactive platinum complex, a succinimidyl ester of a carboxylic acid, a haloacetamide, a hydrazine, an isothiocyanate, a maleimide group or an azidoperfluorobenzamido group.

38. A kit, comprising:
a) a quenching compound of the formula

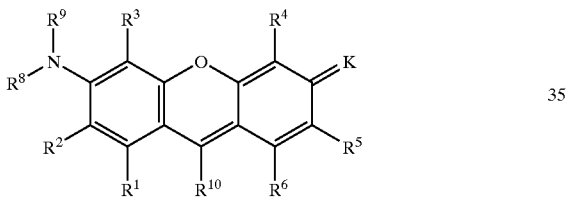

wherein
$R^1$ is H; $R^6$ is H;
$R^2$, $R^3$, $R^4$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$
where X is H or a counterion;
or $R^1$ taken in combination with $R^2$, or $R^6$ taken in combination with $R^5$ is a fused six-membered aromatic ring;
$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or —L—$S_c$; or one or more of $R^8$ and $R^9$ is a Q moiety; or $R^8$ taken in combination with $R^9$ forms a saturated 5- or 6-membered heterocycle that is optionally fused to a-Q moiety and said heterocycle is optionally further substituted by methyl, carboxylic acid, a salt of carboxylic acid, a carboxylic acid ester of a $C_1$–$C_6$ alkyl, or by —L—$S_c$;
wherein each Q moiety is 1–4 aromatic or heteroaromatic rings that is optionally substituted by halogen, cyano, sulfo, alkali or ammonium salt of sulfo, carboxy, alkali or ammonium salt of carboxy, nitro, alkyl, perfluoroalkyl, alkoxy, alkylthio, amino, monoalkylamino, dialkylamino; alkylamido; or is substituted by —L—$S_c$; wherein each heteroaromatic ring in Q is a 5- or 6-membered aromatic heterocycle having 1 to 3 heteroatoms selected from the group consisting of O, N or S in any combination; and when Q is 2–4 rings, said 2–4 rings are fused to each other; and K is O or $N^+R^{18}R^{19}$;
wherein $R^{18}$ and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or —L—$S_c$; or one or more of $R^{18}$ and $R^{19}$ is a Q moiety; or $R^{18}$ taken in combination with $R^{19}$ forms a saturated heterocyclic ring that is a morpholine, a pyrazine, or a piperazine, that is optionally substituted by methyl, sulfonic acid, a salt of sulfonic acid, carboxylic acid, a salt of carboxylic acid, or a carboxylic acid ester of a $C_1$–$C_6$ alkyl; or $R^{18}$ taken in combination with $R^{19}$ forms a saturated 5- or 6-membered heterocycle that is a piperidine, or a pyrrolidine that is optionally fused to a Q moiety, and the heterocycle is optionally further substituted by methyl, carboxylic acid; a salt of carboxylic acid, a carboxylic acid ester of a $C_1$–$C_6$ alkyl, or by —L—$S_c$;
$R^{10}$ is H, CN, a carboxylic acid, a salt of carboxylic acid, or a carboxylic acid ester of a $C_1$–$C_6$ alcohol; or $R^{10}$ is a saturated or unsaturated $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino, the alkyl groups of which have 1–6 carbons; or $R^{10}$ has the formula

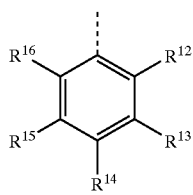

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid; or one of $R^{12}$, $R^{13}$, $R^{14}$, $R^{15}$ and $R^{16}$ is —L—$S_c$;

provided that at least one of $R^8$, $R^9$, $R^{18}$, and $R^{19}$ is, or is fused to, a Q moiety; and further provided that at least one of $R^8$, $R^9$, $R^{12}$, $R^{13}$, $R^{14}$, $R^{15}$, $R^{16}$, $R^{18}$, or $R^{19}$ is —L—$S_c$; or at least one Q moiety is substituted by —L—$S_c$; wherein L is a covalent linkage; and $S_c$ is a conjugated substance; and b) a luminophore donor.

39. A kit, as claimed in claim 38, further comprising an additional detection reagent.

40. A kit, as claimed in claim 38, further comprising one or more luminescence standards.

41. A kit, as claimed in claim 38, wherein said quenching compound and said luminophore are covalently bound to the same conjugated substance, $S_c$.

42. A kit, as claimed in claim 41, wherein said conjugated substance is an oligonucleotide, nucleic acid polymer, peptide or protein.

43. A kit, as claimed in claim 38, wherein $S_c$ is a member of a specific binding pair, and said luminophore donor is covalently bound to the complementary member of said specific binding pair.

44. A kit, as claimed in claim 33, wherein said quenching compound has the formula

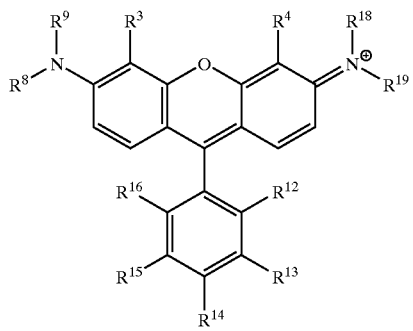

wherein
$R^{12}$ is —L—$S_c$; and
$S_c$ is an oligonucleotide, nucleic acid polymer, peptide or protein.

* * * * *